US012322510B2

(12) United States Patent
Nobrega et al.

(10) Patent No.: US 12,322,510 B2
(45) Date of Patent: Jun. 3, 2025

(54) SYSTEMS AND METHODS FOR PROVIDING ACTIVE CONTRACTION PROPERTIES OF THE MYOCARDIUM USING LIMITED CLINICAL METRICS

(71) Applicant: UNIVERSITY OF SOUTH FLORIDA, Tampa, FL (US)

(72) Inventors: Igor Nobrega, Tampa, FL (US); Wenbin Mao, Tampa, FL (US)

(73) Assignee: UNIVERSITY OF SOUTH FLORIDA, Tampa, FL (US)

(*) Notice: Subject to any disclaimer, the term of this patent is extended or adjusted under 35 U.S.C. 154(b) by 305 days.

(21) Appl. No.: 18/175,337

(22) Filed: Feb. 27, 2023

(65) Prior Publication Data

US 2023/0274837 A1  Aug. 31, 2023

Related U.S. Application Data

(60) Provisional application No. 63/314,284, filed on Feb. 25, 2022.

(51) Int. Cl.
*G16H 50/20* (2018.01)
(52) U.S. Cl.
CPC .................. *G16H 50/20* (2018.01)
(58) Field of Classification Search
None
See application file for complete search history.

(56) References Cited

U.S. PATENT DOCUMENTS

| | | | |
|---|---|---|---|
| 11,024,404 B2 | 6/2021 | Mihalef et al. | |
| 2008/0319308 A1* | 12/2008 | Tang | A61B 5/055 600/416 |
| 2010/0113945 A1* | 5/2010 | Ryan | A61B 5/053 600/486 |
| 2016/0228190 A1* | 8/2016 | Georgescu | A61B 34/10 |
| 2017/0172518 A1* | 6/2017 | Vallee | A61B 5/029 |
| 2019/0197199 A9* | 6/2019 | Mansi | G16H 50/50 |
| 2020/0100768 A1* | 4/2020 | Torres | A61B 8/0883 |

(Continued)

FOREIGN PATENT DOCUMENTS

DE  102021107604 A1 * 9/2022

OTHER PUBLICATIONS

Cai et al. Surrogate models based on machine learning methods for parameter estimation of left ventricular myocardium, R. Soc. Open Sci. 8: 201121 https://doi.org/10.1098/rsos.201121.*

(Continued)

*Primary Examiner* — David J Stoltenberg
(74) *Attorney, Agent, or Firm* — Quarles & Brady LLP

(57) ABSTRACT

A deep learning model can be used for the identification of active contraction properties of the myocardium using limited clinical methods. A method for identifying the active contraction properties can include inputting a plurality of clinical metrics into a deep learning model. The method can further include inputting a representation of a cardiac cycle through a pressure volume-loop into the deep learning model. The deep learning model can include a first process layer with a first intermediate output and a second process layer that receives the first intermediate output as a first intermediate input. The method can further include outputting one or more contraction properties of the myocardium.

20 Claims, 30 Drawing Sheets
(29 of 30 Drawing Sheet(s) Filed in Color)

(56) References Cited

U.S. PATENT DOCUMENTS

| | | | |
|---|---|---|---|
| 2020/0226757 A1* | 7/2020 | Hare, II | G16H 40/63 |
| 2022/0068481 A1* | 3/2022 | Maessen | G16H 50/20 |
| 2022/0101530 A1* | 3/2022 | Trayanova | G16H 50/20 |
| 2023/0149089 A1* | 5/2023 | Trayanova | G16H 20/40 705/2 |
| 2023/0187052 A1* | 6/2023 | Chen | G16H 50/30 382/268 |
| 2023/0274837 A1 | 8/2023 | Nobrega et al. | |
| 2024/0423553 A1* | 12/2024 | Lloyd | A61B 5/7425 |

OTHER PUBLICATIONS

Dabiri et al. Prediction of Left Ventricular Mechanics Using Machine Learning, Front Phys. Sep. 2019 ; 7: . doi: 10.3389/fphy.2019.00117.*

Bayer et al. A Novel Rule-Based Algorithm for Assigning Myocardial Fiber Orientation to Computational Heart Models, Ann Biomed Eng. Oct. 2012 ; 40(10): 2243-2254. doi: 10.1007/s10439-012-0593-5.*

Courville, I.G.a.Y.B.a.A., Deep Learning. 2016: MIT Press. [Book].

Alcidi, Gian Marco, et al. "Normal reference values of multilayer longitudinal strain according to age decades in a healthy population: A single-centre experience." European Heart Journal-Cardiovascular Imaging 19.12 (2018): 1390-1398.

Antonini-Canterin, Francesco, et al. "The ventricular-arterial coupling: from basic pathophysiology to clinical application in the echocardiography laboratory." Journal of cardiovascular echography 23.4 (2013): 91.

Asner, Liya, et al. "Estimation of passive and active properties in the human heart using 3D tagged MRI." Biomechanics and modeling in mechanobiology 15 (2016): 1121-1139.

Avazmohammadi, Reza, et al. "An integrated inverse model-experimental approach to determine soft tissue three-dimensional constitutive parameters: application to post-infarcted myocardium." Biomechanics and modeling in mechanobiology 17 (2018): 31-53, pp. 1-43.

Barbarotta, Luca, et al. "A transmurally heterogeneous orthotropic activation model for ventricular contraction and its numerical validation." International journal for numerical methods in biomedical engineering 34.12 (2018): e3137.

Bayer, Jason D., et al. "A novel rule-based algorithm for assigning myocardial liber orientation to computational heart models." Annals of biomedical engineering 40 (2012): 2243-2254.

Benjamin, E., et al. (2019) Heart Disease and Stroke Statistics—2019 Update: A Report From the American Heart Association. Circulation, 2019.

Bogaert, Jan, and Frank E. Rademakers. "Regional nonuniformity of normal adult human left ventricle." American Journal of Physiology—Heart and Circulatory Physiology 280.2 (2001): H610-H620.

Boyett, M. R., J. E. Frampton, and M. S. Kirby, "The length, width and volume of isolated rat and ferret ventricular myocytes during twitch contractions and changes in osmotic strength." Experimental Physiology: Translation and Integration 76.2 (1991): 269-270.

Carreras, F., et al. "Left ventricular torsion and longitudinal shortening: two fundamental components of myocardial mechanics assessed by tagged cine-MRI in normal subjects." The international journal of cardiovascular imaging 28 (2012): 273-284.

Chabiniok, Radomir, et al. "Estimation of tissue contractility from cardiac cine-MRI using a biomechanics heart model." Biomechanics and modeling in mechanobiology 11 (2012): 609-630.

Cheng, J., & Zhang, L. T. (2018). A general approach to derive stress and elasticity tensors for hyperelastic isotropic and anisotropic biomaterials. International journal of computational methods, 15(04), 1850028.

Chengode, Suresh, "Left ventricular global systolic function assessment by echocardiography."Annals of cardiac anaesthesia 19.Suppl 1 (2016): S26.

Cilla, Myriam, et al. "On the use of machine learning techniques for the mechanical characterization of soft biological tissues." International journal for numerical methods in biomedical engineering 34.10 (2018): e3121.

Dabiri, Yaghoub, et al. "Method for calibration of left ventricle material properties using three-dimensional echocardiography endocardial strains." Journal of biomechanical engineering 141.8 (2019): pp. 091007-1-091007-10.

Dabiri, Yaghoub, et al. "Application of feed forward and recurrent neural networks in simulation of left ventricular mechanics." Scientific Reports 10.1 (2020): 22298, pp. 1-11.

Di Donato, Marisa, et al. "Left ventricular geometry in normal and post-anterior myocardial infarction patients: sphericity index and 'new'conicity index comparisons." European journal of cardio-thoracic surgery 29.Supplement_1 (2006): S225-S230.

Doersch, Carl. (2016). Tutorial on Variational Autoencoders. stat, 1050, 13; pp. 1-23.

Dokos, Socrates, et al. "Shear properties of passive ventricular myocardium." American Journal of Physiology—Heart and Circulatory Physiology 283.6 (2002): H2660-H2659.

Dumesnil, J. G., & Shoucri, R. M. (1991). Quantitative relationships between left ventricular ejection and wall thickening and geometry. Journal of applied physiology, 70(1), 48-54.

Edvardsen, Thor, and Kristina H. Haugaa. "Imaging assessment of ventricular mechanics." Heart 97.16 (2011): 1349-1356.

Everaars, Henk, et al. "Strain analysis is superior to wall thickening in discriminating between infarcted myocardium with and without microvascular obstruction." European Radiology 28 (2018): 6171-6181.

Finsberg, Henrik, et al. "Estimating cardiac contraction through high resolution data assimilation of a personalized mechanical model." Journal of computational science 24 (2018): 86-90.

Finsberg, Henrik, et al. "Efficient estimation of personalized biventricular mechanical function employing gradient-based optimization." International journal for numerical methods in biomedical engineering 34.7 (2018): e2982, pp. 1-20.

Galati F. Ourselin S, Zuluaga MA (2022) From Accuracy to Reliability and Robustness in Cardiac Magnetic Resonance Image Segmentation: A Review. Applied Sciences 12. doi:10.3390/app12083936. pp. 1-19.

Galderisi, Maurizio, et al. "Standardization of adult transthoracic echocardiography reporting in agreement with recent chamber quantification, diastolic function, and heart valve disease recommendations: an expert consensus document of the European Association of Cardiovascular Imaging." European Heart Journal—Cardiovascular Imaging 18.12 (2017): 1301-1310.

Gasser, T. C., Ogden, R. W., & Holzapfel, G. A. (2006). Hyperelastic modelling of arterial layers with distributed collagen fibre orientations. Journal of the royal society interface, 3(6), 16-35.

Gao, H., et al. "Parameter estimation in a Holzapfel-Ogden law for healthy myocardium." Journal of engineering mathematics 95 (2015): 231-248.

Germano, Guido, et al. "Automatic quantification of ejection fraction from gated myocardial perfusion SPECT." Journal of Nuclear Medicine 36.11 (1995): 2138-2147.

Gilbert, S.H., et al., Regional localisation of left ventricular sheet structure: integration with current models of cardiac libre, sheet and band structure. 2007, Elsevier Science B.V., Amsterdam.: Netherlands, p. 231.

Guan, Debao, et al. "On the AIC-based model reduction for the general Holzapfel-Ogden myocardial constitutive law." Biomechanics and Modeling in Mechanobiology 18 (2019): 1213-1232.

Gökiepe, Serdar, el al. "Computational modeling of passive myocardium." International Journal for Numerical Methods in Biomedical Engineering 27.1 (2011): 1-12.

Goldberger, Ary L., et al. "PhysioBank, PhysioToolkit, and PhysioNet: components of a new research resource for complex physiologic signals." circulation 101.23 (2000): e215-e220.

Hadjicharalambous, Myrianthi, et al. "Analysis of passive cardiac constitutive laws for parameter estimation using 3D tagged MRI." Biomechanics and modeling in mechanobiology 14 (2016): 807-828.

(56) References Cited

OTHER PUBLICATIONS

Halevy, Alon, Peter Norvig, and Fernando Pereira. "The unreasonable effectiveness of data." IEEE intelligent systems 24.2 (2009): 8-12.

Hasaballa, A. I. M. (2014). Finite Element Analysis of Left Ventricle Motion and Mechanical Properties in Three Dimensions. University of Malaya (Malaysia).[Book].

Heldt, Thomas, et al. "CVSim: an open-source cardiovascular simulator for teaching and research." The open pacing, electrophysiology & therapy journal 3 (2010): 46.

Hochreiter, Sepp, and Jürgen Schmidhuber. "Long short-term memory." Neural computation 9.8 (1997): 1735-1780.

Hoerig, C., Ghaboussi, J., & Insana, M. F. (2017). An information-based machine learning approach to elasticity imaging. Biomechanics and modeling in mechanobiology, 16, 805-822.

Holzapfel, G. A., & Ogden, R. W. (2009). Constitutive modelling of passive myocardium: a structurally based framework for material characterization. Philosophical Transactions of the Royal Society A: Mathematical, Physical and Engineering Sciences, 367(1902), 3445-3475.

Huang, Dengpeng, et al. "A machine learning based plasticity model using proper orthogonal decomposition." Computer Methods in Applied Mechanics and Engineering 365 (2020): 113008; pp. 1-33.

Hunter, Peter, et al. "A vision and strategy for the virtual physiological human in 2010 and beyond." Philosophical Transactions of the Royal Society A: Mathematical, Physical and Engineering Sciences 368.1920 (2010): 2596-2614.

Kelly, D., et al. "Gene expression of stretch-activated channels and mechanoelectric feedback in the heart." Clinical and experimental pharmacology and physiology 33.7 (2006): 642-648.

Kingma, D. P., & Welling, M. (2014). Auto-Encoding Variational Bayes. stat, 1050, 1; pp. 1-14.

Kohl, P., Hunter, P., & Noble, D. (1999). Stretch-induced changes in heart rate and rhythm: clinical observations, experiments and mathematical models. Progress in biophysics and molecular biology, 71(1), 81-138.

Kononenko, I. (2001). Machine learning for medical diagnosis: history, state of the art and perspective. Artificial Intelligence in medicine, 23(1), 1-25.

Nagata, Yasufumi, et al. "Normal range of myocardial layer-specific strain using two-dimensional speckle tracking echocardiography." PLoS One 12.6 (2017): e0180584; 1-16.

Warriner. David R., et al. "Closing the loop: modelling of heart failure progression from health to end-stage using a meta-analysis of left ventricular pressure-volume loops." PLoS One 9.12 (2014): e114163; 1-19.

Zhang, Xiaoyan, et al. "Evaluation of a novel finite element model of active contraction in the heart." Frontiers in physiology 9 (2018): 425.

Kovacheva, Ekaterina, et al. "Estimating cardiac active tension from wall motion—An inverse problem of cardiac biomechanics." International Journal for Numerical Metho is in Biomedical Engineering 37.12 (2021): e3448; pp. 1-22.

LeGrice, I.J., Y. Takayama, and J.W. Covell, Transverse Shear Along Myocardial Cleavage Planes Provides a Mechanism for Normal Systolic Wall Thickening. 1995. United States: American Heart Association Inc.

Liang, L., Liu, M., Martin, C., & Sun, W. (2018). A deep learning approach to estimate stribution: a fast and accurate surrogate of finite-element analysis. Journal of the Royal Society, Interface, 15(138) 844, pp. 1-10. https://doi.org/10.1098/rsif.2017.0844.

Lindsey, Merry L., et al. "Guidelines for measuring cardiac physiology in mice." American Journal of Physiology—Heart and Circulatory Physiology 314.4 (2018): H733-H752.

Lunkenheimer, Paul P., et al. "Three-dimensional architecture of the left ventricular myocardium." The Anatomical Record Part A: Discoveries in Molecular, Cellular, and Evolutionary Biology: An Official Publication of the American Association of Anatomists 288.6 (2006): 565-578.

Maciver, David H., Ismail Adeniran, and Henggul Zhang. "Left ventricular ejection fraction is d mined by both global myocardial strain and wall thickness." IJC Heart & Vasculature 7 (2015): 113-118.

Maas, Steve A., et al. "A plugin framework for extending the simulation capabilities of FEBio." Biophysical journal 115.9 (2018): 1630-1637.

Maas, Steve A., et al. "FEBio: finite elements for biomechanics." (2012): 011005-1-011005-10.

Nelson, H.H.C., Building Machine Learning Pipelines. 1 ed. 2020: O'Reilly Media, Inc. [Book].

Pezzuto, S., Ambrosi, D., & Quarteroni, A. L. F. I. O. (2014). An orthotropic active-strain model for the myocardium mechanics and its numerical approximation. European Journal of Mechanics-A/Solids, 48, 83-96.

Palit, Arnab, et al. "In vivo estimation of passive biomechanical properties of human myocardium." Medical & biological engineering & computing 66 (2018): 1615-1631.

Rossi, S., et al. (2012). Orthotropic active strain models for the numerical simulation of cardiac biomechanics. International journal for numerical methods in biodmedical engineering, 28(6-7), 761-788.

Schmid, Holger, et al. "Myocardial material parameter estimation: a non-homogeneous finite element study from simple shear tests." Biomechanics and modeling in mechanobiology 7 (2008): 161-162.

Slinde, Gaute Aasen. Numerical Modelling and Analysis of the Left Ventricle. MS thesis. NTNU, 2015, p. 1-137.

Stokke, Thomas M., et al. "Geometry as a confounder when assessing ventricular systolic function: comparison between ejection fraction and strain." Journal of the American College of Cardiology 70.8 (2017): 942-954.

Støylen, Asbjørn, et al. "Left ventricular longitudinal shortening: relation to stroke volume and ejection fraction in ageing, blood pressure, body size and gender in the HUNT3 study." Open Heart 7.2 (2020): e001243; 1-10.

Talbot, S.R.R.V.T., Vascular system. 2019, Salem Press. [Book].

Valliappa Lakshmanan, S.R.M.M., Machine Leaning Design Patterns. 1 ed. 2020: O'Reilly Media Inc. [Book].

Vincent, Pascal, et al. "Stacked denoising autoencoders: Learning useful representations in a deep network with a local denoising criterion." Journal of machine learning research 11.12 (2010); 3371-3408.

Voigt, Jens-Uwe, and Marta Cvijic. "2-and 3-dimensional myocardial strain in cardiac health and disease." JACC: Cardiovascular Imaging 12.9 (2019): 1849-1863.

Voigt, Jens-Uwe, et al. "Definitions for a common standard for 2D speckle tracking echocardiography: consensus document of the EACVI/ASE/Industry Task Force to standardize deformation imaging." European Heart Journal—Cardiovascular Imaging 16.1 (2015): 1-11.

Wang, H. M., et al. "Structure-based finite strain modelling of the human left ventricle in diastole." International journal for numerical methods in biomedical engineering 29.1 (2013): 83-103.

Wong, J., & Kuhl, E. (2014). Generating fibre orientation maps in human heart models using Poisson interpolation. Computer methods in biomechancis and biomedical engineering. 17(11), 1217-1226.

Yin, Frank CP, et al. "Quantification of the mechanical properties of noncontracting canine myocardium under simultaneous biaxial loading." Journal of biomechanics 20.6 (1987): 577-689.

Jashan, Haki, et al. "Normal ranges of left ventricular strain in children: a meta-analysis." Cardiovascular ultrasound 13 (2015): 1-16.

Jolly, Marie-Pierre, et al. "Automated assessments of circumferential strain from cine CMR correlate with LVEF declines in cancer patients early after receipt of cardio-toxic chemotherapy." Journal of Cardiovascular Magnetic Resonance 19 (2017): 1-12.

Kerkhof, Peter LM, et al. "Ejection fraction as related to basic components in the left and right ventricular volume domains." International journal of cardiology 265 (2018): 105-110.

Kirchdoerfer, T., & Ortiz, M. (2016). Data-driven computational mechanics. Computer Methods in Applied Mechanics and Engineering, 304, 81-101.

(56) References Cited

OTHER PUBLICATIONS

Last, C.S.S.R.J., Last's anatomy : regional and applied. 12 ed. 2006: Churchill Livingstone;. 560. [Book].

Litjens, Geert, et al. "State-of-the-art deep lea ovascular image analysis." JACC: Cardiovascular imaging 12.8 Part 1 (2019): 1549-1565.

Mao, Wenbin, et al. "Fully-coupled fluid-structure interaction simulation of the aortic and mitral valves in a realistic 3D left ventricle model." PloS one 12.9 (2017): e0184729.

Marx, Laura, et al. "Robust and efficient fixed-point algorithm for the inverse elastostatic problem to identify myocardial passive material parameters and the unloaded reference configuration." Journal of computational physics 463 (2022): 111266; 1-25.

Matthews, Stephen D., et al. "Myocardial contraction fraction: a volumetric measure of myocardial shortening analogous to strain." Journal of the American College of Cardiology 71.2 (2018): 255-256.

Mueller-Freitag, M., 10 Data Acquisition Strategies for Startups. 2016: Medium, [Book].

Moore, Christopher C., et al. "Three-dimensional systolic strain patterns in the normal human left ventricle: characterization with lagged MR imaging. " Radiology 214.2 (2000): 453-468.

Mora, Vicente, et al. "Comprehensive assessment of left ventricular myocardial function by two-dimensional speckle-tracking echocardiography." Cardiovascular ultrasound 16 (2018): 1-8.

Regazzoni, F., L. Dedè, and A. Quarteroni, "Machine learning of multiscale active force generation models for the efficient simulation of cardiac electromechanics." Computer Methods in Applied Mechanics and Engineering 370 (2020): 113268; 1-30.

Romaszko, Lukasz, et al. "Neural network-based left ventricle geometry prediction from CMR images with application in biomechanics." Artificial Intelligence in Medicine 119 (2021): 102140; 1-20.

Rossi, Simone, et al. "Thermodynamically consistent orthotropic activation model capturing ventricular systolic wall thickening in cardiac electromechanics." European Journal of Mechanics-A/Solids 48 (2014): 128-142.

Quarteroni, Alfio, et al. "Integrated heart—coupling multiscale and multiphysics models for the simulation of the cardiac function." Computer Methods in Applied Mechanics and Engineering 314 (2017): 345-407.

Smiseth, Otto A., et al. "Myocardial strain imaging: how useful is it in clinical decision making?." European heart journal 37.15 (2016): 1196-1207.

Seemann, Felicia, et al. "Noninvasive quantification of pressure-volume loops from brachial pressure and cardiovascular magnetic resonance." Circulation: Cardiovascular Imaging 12.1 (2019): e008493.

Sermesant, Maxime, et al. "Cardiac function estimation from MRI using a heart model and data assimilation: advances and difficulties." Medical image analysis 10.4 (2006): 642-656.

Spinelli, Letizia, et al. "Left ventricular radial strain impairment precedes hypertro n Anderson-Fabry disease." The International Journal of Cardiovascular Imaging 36 (2020): 1466-1476.

Tang, Dalin, et al. "Image-based patient-specific ventricle models with fluid-structure interaction for cardiac function assessment and surgical design optimization." Progress in pediatric cardiology 30.1-2 (2010): 51-62.

Tsugu, Toshimitsu, et al. "Echocardiographic reference ranges for normal left ventricular layer-specific strain: results from the EACVI NORRE study." European Heart Journal—Cardiovascular Imaging 21.8 (2020): 896-906.

Viceconti, Marco, and Peter Hunter. "The virtual physiological human: ten years after." Annual review of biomedical engineering 18 (2016): 103-123.

Weidman, S., Deep Learning from Scratch, 1 ed. 2019: O'Reilly Media, Inc. 236. [Book].

* cited by examiner

SYSTEMS AND METHODS FOR PROVIDING ACTIVE CONTRACTION PROPERTIES OF THE MYOCARDIUM USING LIMITED CLINICAL METRICS

CROSS-REFERENCE TO RELATED APPLICATIONS

This application claims priority under 35 U.S.C. § 119 to U.S. Provisional Patent Application No. 63/314,284 filed on Feb. 25, 2022, the entire contents of which are incorporated herein by reference.

BACKGROUND

Cardiovascular diseases are one of the most critical public health concerns, which affect millions of people each year and continue to be the leading cause of death globally. It is generally useful to have an understanding and an ability to comprehend the many components of the human heart, as well as other biological tissues. Increasing experimental, theoretical, and computational knowledge of the fundamental mechanisms underlying heart function will significantly assist in creating and refining innovative medicine and prognostic approaches.

SUMMARY

Some examples of the present disclosure provide a method for providing active contraction properties of a myocardium. The method can include inputting a plurality of clinical metrics into a deep learning model. The method can further include inputting a representation of a cardiac cycle through a pressure-volume loop into the deep learning model. The deep learning model can include a first process layer with a first intermediate output and a second process layer that receives the first intermediate output as a first intermediate input. The method can further include outputting one or more contraction properties of the myocardium.

In some examples, a method of data generation for training, validating, or testing a model for outputting properties of a myocardium is provided. The method can include inputting an initial pressure-volume loop into a training model. The method can also include inputting initial fiber orientations into the training model. The method can also include combining pressure and volume values with fiber orientations in a first intermediate model of the training model to produce geometric characteristics to form synthetic clinical metrics. The method can further include combining pressure and volume values with fiber orientations in a second intermediate model of the training model to generate a synthetic gamma waveform. The method can also include supplying the pressure-volume loop and the synthetic clinical metrics to a deep learning model of the training model.

In some examples, a method of using a constitutive model in a clinical application when limited clinical data is available is provided. The method can include extracting constitutive model parameters from basic clinical measures. The basic clinical measures can include a pressure-volume (PV) loop and measurements in only two timesteps of, for instance, a left ventricle. The constitutive model can be configured to correlate applied forces with a material's mechanical response by incorporating characteristics of morphology of tissue into its internal composition to provide tissue behavior analysis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
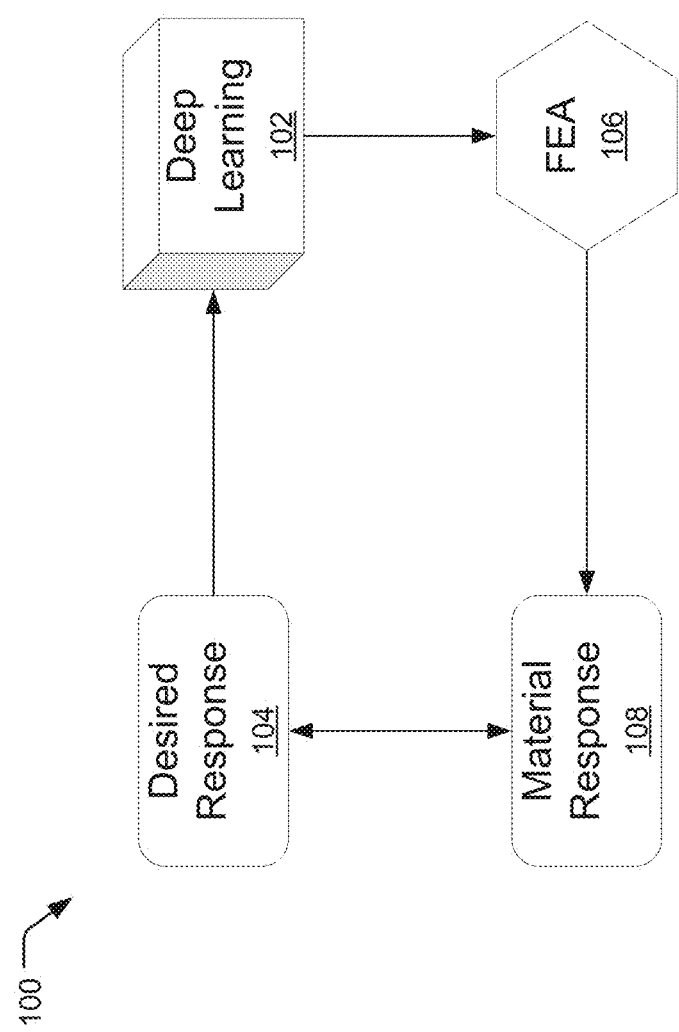
FIG. 1 is a schematic illustration of a method for identifying and predicting the behavior of a left ventricular myocardium according to an embodiment of the disclosure.

The concepts disclosed in this discussion are described and illustrated with reference to exemplary arrangements. These concepts, however, are not limited in their application to the details of construction and the arrangement of components in the illustrative embodiments and are capable of being practiced or being carried out in various other ways. The terminology in this document is used for the purpose of description and should not be regarded as limiting. Words such as "including," "comprising," and "having" and variations thereof as used herein are meant to encompass the items listed thereafter, equivalents thereof, as well as additional items.

While the methodologies disclosed herein may be embodied in many different forms, several specific embodiments are discussed herein with the understanding that the embodiments described in the present disclosure are to be considered only exemplifications of the principles described herein, and the disclosed technology is not intended to be limited to the examples illustrated.

As briefly described above, cardiovascular diseases are one of the most critical public health concerns, which affect millions of people each year and continue to be the leading cause of death globally. As reported by the American Heart Association (AHA), the prevalence of cardiovascular diseases (CVD) in young adults (aged 20 to 30) exceeds 48% and continues to rise with age. This scenario surpasses the number of deaths caused by different types of cancer and other respiratory diseases, which account for nearly one in every three deaths in the United States.

To forestall an uncontrollable increase in these numbers, it is important to comprehend the many components of the human heart, as well as other biological tissues. Increasing experimental, theoretical, and computational knowledge of the fundamental mechanisms underlying heart function will significantly assist in creating and refining innovative medicine and prognostic approaches. Further, technological improvements have paved the way for identifying essential mechanical characteristics of soft tissues and their influence on their physiological functions. The living tissue's elastic properties can be employed to discover possible symptoms of sickness or physiological issues; for instance, these properties can be used to characterize the regions of inflammation, edema, hypertrophy, and fibrosis caused by different disease processes.

The field of continuum mechanics of hyper-elastic material can permit the development of highly descriptive mathematical analysis and computational models capable of accurately capturing the mechanical characteristics of soft tissue. The constitutive models correlate applied forces with the material's mechanical response by incorporating characteristics of the morphology of the tissue into its internal composition, which allows for accurate reinterpretation and analysis of tissue behavior. Due to the composition of biological tissues, assessing mechanical characteristics can be challenging. The mathematical modeling of living cardiovascular tissue faces myriad difficulties due to anisotropic material behavior, nonlinear equations, geometric complexity, heterogeneity, and challenging in vivo observations. Other limitations are imposed by diverse physiological processes, mechanical stresses, and boundary conditions. Additionally, the myocardium tissue manifests divergent behavioral patterns in active and passive instances, exposing them to indeterminate residual stresses and significantly increasing mechanical response variance.

Taking these constraints into account, as well as the fact that conducting constitutive modeling often requires substantial computer resources and time, the outcome of varied constitutive models without proper parameter selection is generic and does not represent patient-specific analyses. In fact, rather than performing clinically relevant investigations, most "heart simulations" are designed to train cardiologists and evaluate underlying theoretical concepts. The advantages and extensive analyses revealed by constitutive models are not fully utilized in clinical settings and have yet to be integrated into routine medical operations.

The advancement of sophisticated analytics, such as deep learning methods and high-performance computational science, has sparked interest in data-driven computational modeling as a method of obtaining quick and reliable observations of complicated systems. In general, informational models can interpret hidden patterns between input and output via repeated training on high-quality experimental data. The development of deep learning models in conjunction with constitutive analysis represents a feasible and advantageous opportunity for conducting further clinical studies using non-invasive procedures in realistic patient-specific settings.

Due to the immediacy of this methodology, complex systems are not entirely reliant on a predetermined set of equations, which reduces the occurrence of extraneous constraints and broadens their practical applications. The linkages between clinical-data settings and theoretical constitutive models are reduced to internal model inferences, allowing for direct assessment of the effect of various data on the model's outcome and permitting an extensive clinical perspective to be conducted. Furthermore, physiological interpretations remain within the scope of the model since it is developed based on the underlying constitutive laws established from the training data.

In general, technological breakthroughs have enhanced our understanding of myocardial mechanics and physiological responses to detect early disease indicators. Using constitutive models to represent myocardium structure is critical for understanding the intricacies of such complex tissues. Conventional models have been developed to depict both passive response and active contraction of myocardium, however they require careful adjustment of material parameters for patient-specific scenarios and substantial time and computing resources. Thus, most models are unsuitable for employment outside of research.

Deep learning (DL) has sparked interest in data-driven computational modeling for complex system analysis. We developed a DL model for assessing and forecasting the behavior of an active contraction model of the left ventricular (LV) myocardium under a patient-specific clinical setting. Our original technique analyzes a context in which clinical measures are limited: as model input, just a handful of clinical parameters and a pressure-volume (PV) loop are required. This technique aims to bridge the gap between theoretical calculations and clinical applications by allowing doctors to use traditional metrics without administering additional data and processing resources.

Our DL model's main objectives are to produce a waveform of active contraction property that properly portrays patient-specific data during a cardiac cycle and to estimate fiber angles at the endocardium and epicardium. Our model accurately represented the mechanical response of the LV myocardium for various PV curves, and it applies to both idealized and patient-specific geometries. Integrating artificial intelligence with constitutive-based models allows for the autonomous selection of hidden model parameters and facilitates their application in clinical settings.

Thus, embodiments of the present disclosure provide a deep-learning model, which may be stored in a computer, for evaluating and predicting the behavior of an active contraction model of, for instance, the left ventricular myocardium under patient-specific clinical conditions. Moreover, embodiments of the present disclosure provide exemplary scenarios in which clinical measurements are limited; e.g., only end-diastole and end-systole data are available for the information of a deformed heart. This strategy can minimize the quantity of data demanded to process patient-specific parameters and makes it software- and hardware-independent, enabling clinicians to use routine measurements without the need to manage additional data and computational resources. Furthermore, embodiments of the invention can provide a deep learning model with one or more primary objectives that include generating a parameter waveform that properly determines the active contraction behavior of patient-specific data during a cardiac cycle and estimating the fiber angles at the endocardial and epicardial surfaces.

FIG. 1 illustrates a method 100 for identifying and predicting the behavior of active contraction constitutive model parameters and fiber orientation of the left ventricular myocardium for cardiac cycle using a constitutive-based deep learning model 102 using patient-specific clinical data. According to some embodiments of the invention, the method 100 can start with a desired response 104, which can be determined by clinical metrics. The desired response 104 can be used as an input for the deep learning model 102. The deep learning model 102 can output constitutive model parameters that can be used in a finite element analysis (FEA) 106. The output of the FEA 106 can include a material response 108. The material response 108 can then be compared with the desired response 104 and dictate the training process.

Figure 2:
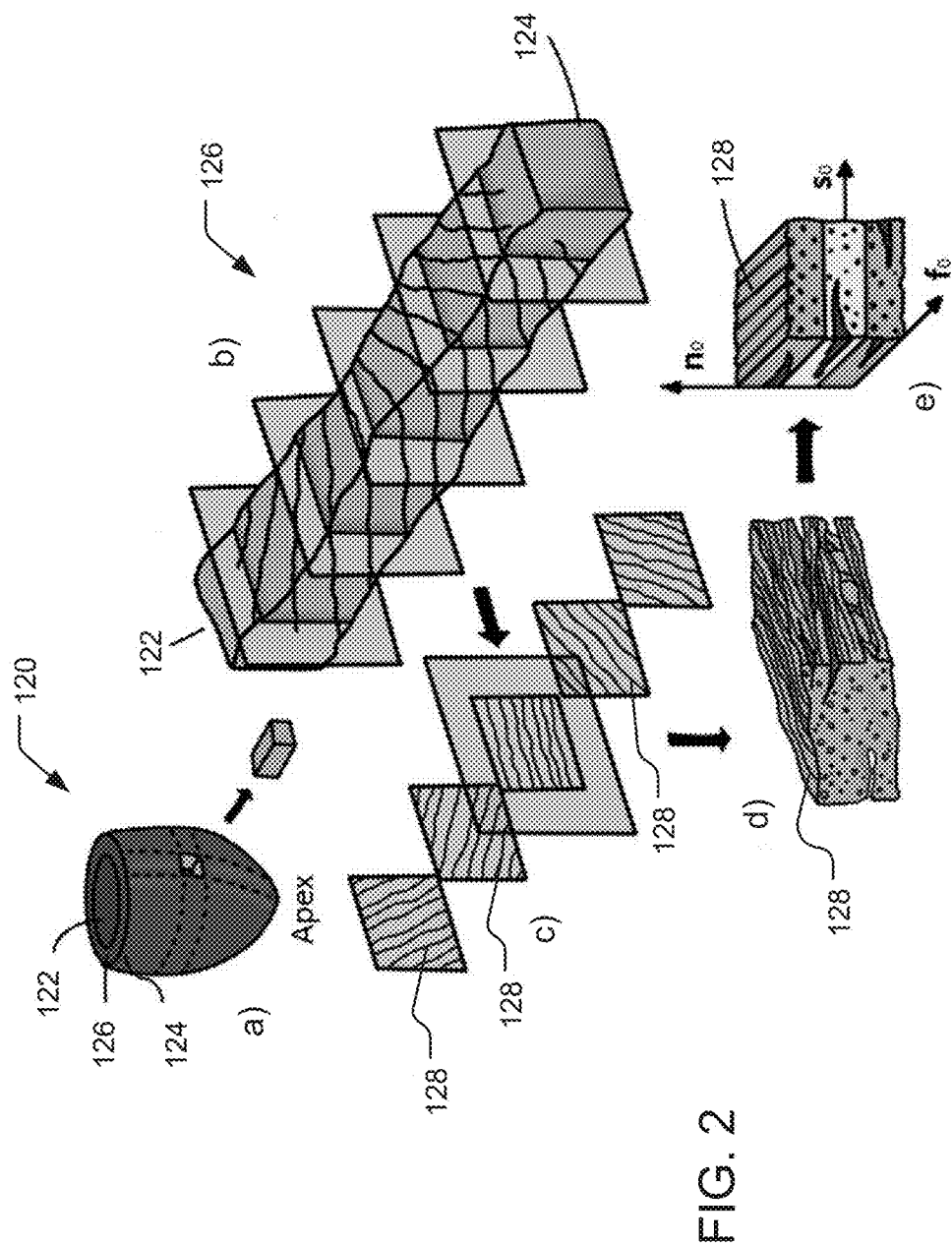
FIG. 2 is a schematic illustration of the mechanical structure of a heart; a) shows a model of a left ventricle of the heart, b) illustrates a representation block of a myocardium wall of the left ventricle, c) shows cross sections along the radial direction of the myocardium wall, d) shows a cross section of the myocardium wall with detailed microstructure, and e) shows local fiber coordinates to describe fiber orientation along the myocardium wall.
Figure 3:
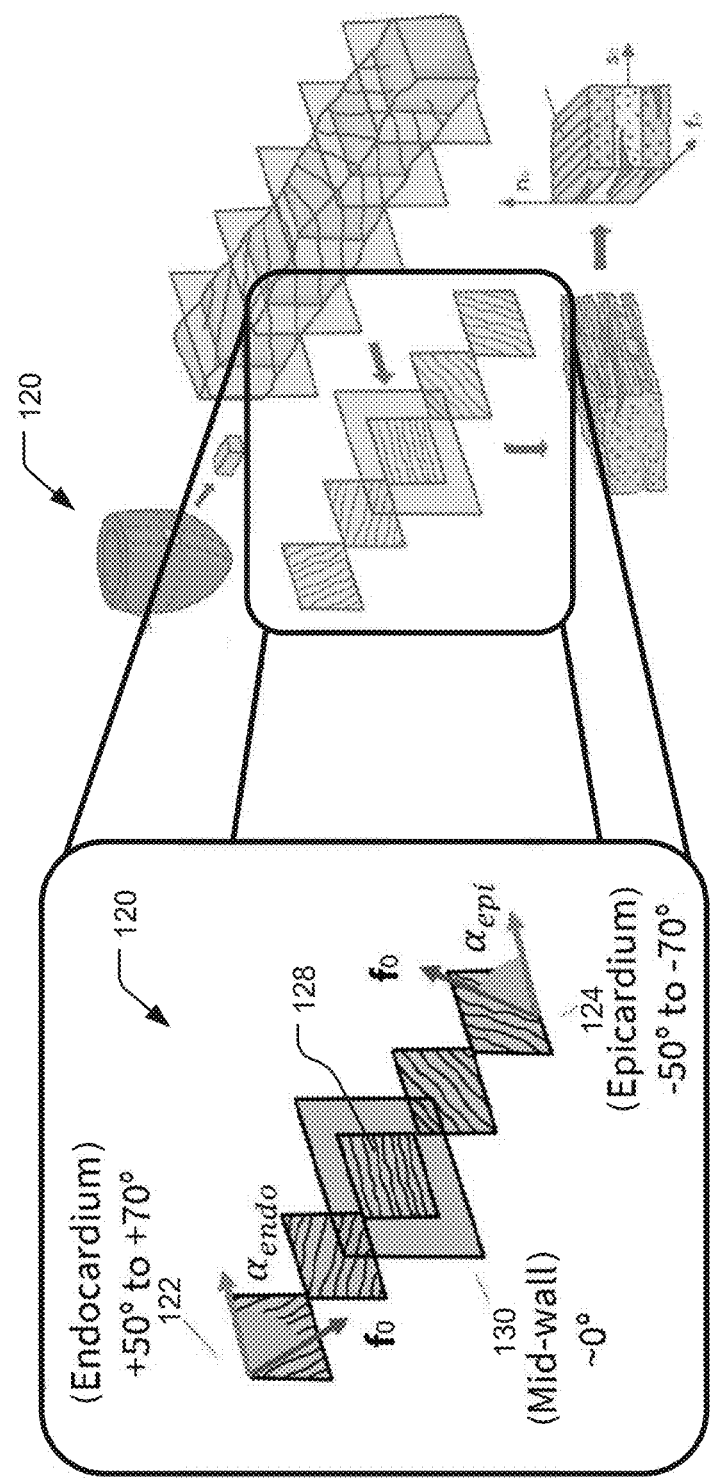
FIG. 3 is a detailed view of the cross section of the myocardium wall of FIG. 2c.

As briefly described above, embodiments of the disclosure provide systems and methods for modeling a mechanical response of, for example, the left ventricular myocardium. To help provide context, FIGS. 2 and 3 illustrate a model of the left ventricular myocardium 120. The left ventricle is responsible for pumping blood throughout the entire circulation system. Thus, the LV is one of the most important components of the heart. The LV 120 can be divided into three layers: the endocardium 122, the epicardium 124, and the myocardium 126. The endocardium 122 is a thin layer composing an inner surface. The epicardium 124 is another thin layer that protects the outer surface of the ventricle. The myocardium 126, which includes the majority of the ventricular wall, includes important structural functions. It is mainly composed of myocytes, a type of muscle cells organized in a layered structure, as shown in FIG. 2b. These layers are organized in a helix orientation along the circumference of the ventricle. As can be seen in FIG. 2e, the fibers 128 can change in orientation from the epicardium 124 to the endocardium 122 from some angle to another angle. The fiber orientation helps to ensure the resilience of the heart to bending and twisting during the cardiac cycle.

FIG. 2b shows a representation block of the myocardium 126 wall and FIG. 2c shows cross-sections along the circumferential direction of the myocardium 126 wall. FIG. 2e illustrates a mean fiber 128 orientation. FIG. 3 illustrates features and fiber 128 angles of the myocardium 126. In particular, the fiber orientation changes from the endocardium 122 through the mid wall 130 and to the epicardium 124. In the illustrated diagram, the fiber orientation is denoted by α.

Figure 4:
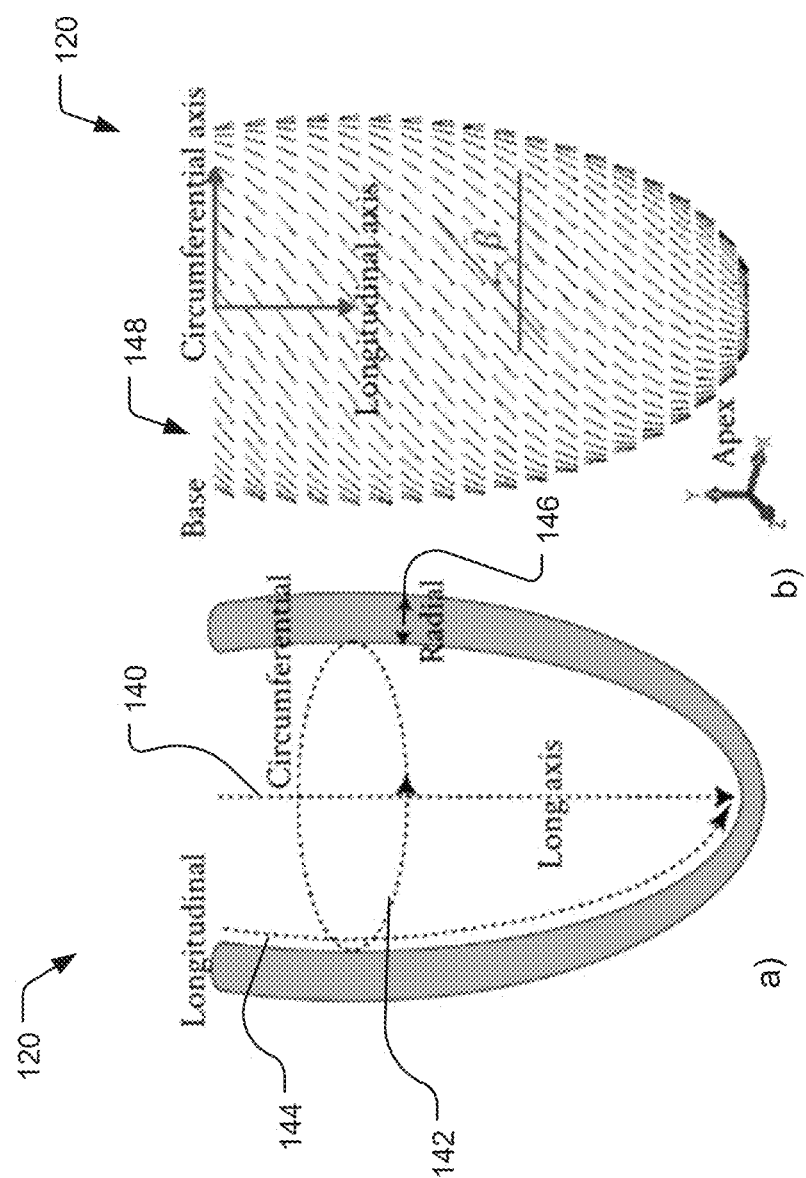
FIG. 4 illustrates a schematic diagram of fiber orientation of a left ventricular myocardium.

FIG. 4 illustrates another diagram of the left ventricular myocardium 120 including a long axis 140, a circumferential axis 142, a longitudinal axis 144, and a radial axis 146. The diagram 120 further defies a base 148 and generally includes a range of fiber orientations that between each of the endocardium, the mid wall, and the epicardium. In general, the orientation of the fibers play an important role in the myocardium contraction. The cylindrical coordinates described with respect to FIG. 4 can be used to help describe the relative orientation of fibers. FIG. 4b illustrates that fiber angle β can be measured between the circumferential 142 and longitudinal 144 axes. The fiber angles normally range from approximately 50 degrees to 70 degrees and positive on the endocardium and negative on the epicardium.

Embodiments herein provide systems and methods for preparing models of, for example, the LV that can include information related to patient-specific fiber orientation. These models can be based off constitutive equations.

In general, constitutive equations provide a complete understanding of physiological and pathological load bearing processes by encapsulating crucial information about the composition and function of the specified biological tissue. Described herein is a comprehensive model of the mechanical behavior of the myocardium that includes both passive and active responses. In this work, we considered the decomposition of the deformation gradient tensor F into two principal domains: the elastic deformation $F_e$ and the active distortion $F_a$ such that:

$$F = F_e F_a \quad (1)$$

As a result, the strain energy density of the passive model is specified solely as a function of Fc, whereas the active deformation $F_a$ is postulated to be the response of entirely dissipative processes. The primary advantage of this method is the ability to employ distinct constitutive models for each designated activity, enabling each domain to be developed and evaluated independently.

Taking this into account, our constitutive model consists of (a) a passive strain invariant-based fiber-reinforced hyperelastic formulation; and (b) a transversely isotropic and locally isochoric active contraction.

Figure 5:
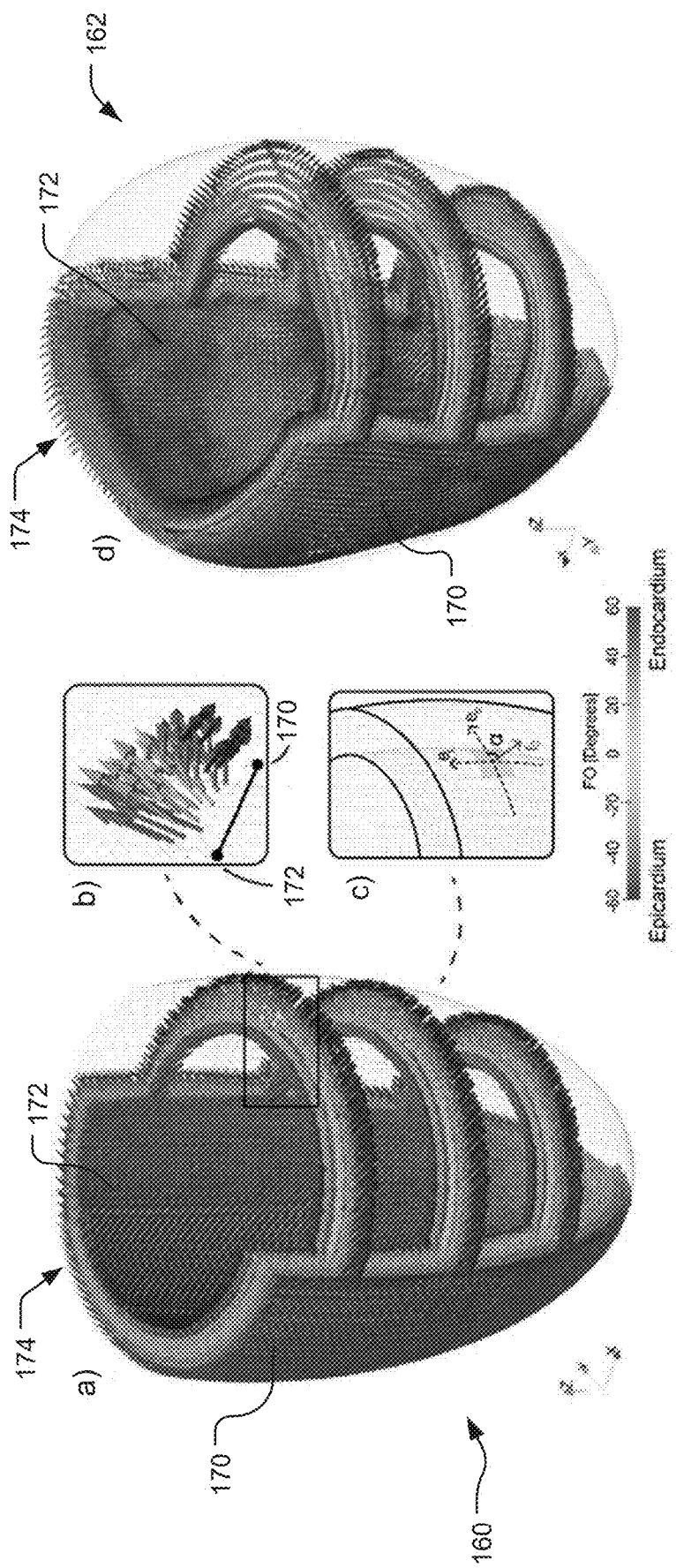
FIG. 5 illustrates models of a left ventricle; a) shows an ideal geometry, b) is an illustrative angle measurement of fiber orientations, c) shows a detailed view of fiber angles in local cylindrical coordinates, and d) shows a patient-specific geometry and fiber orientation of the left ventricle.

A passive model can accurately describe the orthotropic hyper-elastic behavior of the ventricular myocardium by considering the influence of fiber orientation along with different loading conditions. When examining a single cube element, the three local mutually orthogonal axes characterize the basis vectors that define the fiber, $f_0$, sheet (cross-fiber), so, and sheet-normal (normal), no, directions (see, for example, FIGS. 2 and 3). Further, an illustration of $f_0$ is shown in FIG. 5. We can use the right and left Cauchy-Green tensors, denoted as $C = F_e^T F_e$ and $B = F_e F_e^T$ respectively, to define the invariants, $I_1 = tr(C)$, $I_{4f} = f_0 \cdot (Cf_0)$, $I_{4s} = s_0 \cdot (Cs_0)$, and $I_{8fs} = s_0 \cdot (Cf_0)$, where $I_1$ is an isotropic invariant, and the others are orthotropic invariants. As a result, the material is described by the strain-energy function:

$$\psi = \frac{a}{2b} \exp[b(I_1 - 3)] + \sum_{i=f,s} \frac{a_i}{2b_i} \{\exp[b_i(I_{4i} - 1)^2] - 1\} + \frac{a_{fs}}{2b_{fs}} [\exp(b_{fs} I_{8fs}^2) - 1] \quad (2)$$

in which a, b, $a_f$, $a_s$, $b_f$, $b_s$, $a_{fs}$ and $b_{fs}$ are positive material constants with b values being unitless while other parameters are in units of stress. The first component reflects the isotropic contribution, which is the aggregate stiffness of the extracellular matrix. In contrast, the second term indicates additional stiffness along the fiber direction as they are stretched. Notably, these terms significantly contribute to the accumulated energy when the associated directions are under tension. Their involvement, however, is ignored when the fibers are compressed, as the fibers inherently do not sustain compression. The Cauchy stress tensor can be derived from Eq. 2, resulting in Eq. 3 below, where $f = F_e f_0$, $s = F_e s_0$, p is the Lagrange multiplier to ensure incompressibility, and I is the identity tensor.

$$\sigma = a \exp[b(I_1 - 3)]B - pI + 2a_f(I_{4f} - 1)\exp[b_f(I_{4f} - 1)^2] f \otimes f + 2a_s(I_{4s} - 1)\exp[b_s(I_{4s} - 1)^2]s \otimes s + a_{fs} I_{8fs} \exp(b_{fs} I_{8fs}^2)(f \otimes s + s \otimes f) \quad (3)$$

The passive model can include material properties as parameters. Exemplative parameters are shown below in Table 1. The parameters reflect experimental data of myocardium.

The passive model can include material properties as parameters. Exemplative parameters are shown below in Table 1. The parameters reflect experimental data of myocardium.

TABLE 1

Material parameters used for the passive constitutive model of the myocardium.

| a (kPa) | b | $a_f$(kPa) | $b_f$ | $a_s$ (kPa) | $b_s$ | $a_{fs}$ (kPa) | $b_{fs}$ |
|---|---|---|---|---|---|---|---|
| 0.496 | 7.209 | 15.193 | 20.417 | 3.283 | 11.176 | 0.662 | 9.466 |

The second aspect of our constitutive formulation is devoted to portraying the active contraction that emerges due to certain myocardial electrical physiologies. An active strain formulation can be used when considering active contraction. The particular form of $F_a$ is regarded as the result of fully dissipative processes and is predicated on the hypothesis that there is a shortening in the fiber direction $f_0$ and that volume is conserved during active contraction. Moreover, a physiologically driven possibility for $F_a$ is a transversely isotropic and locally isochoric tensor, as implied by the observation that myocytes shorten in the sarcomeres direction during contraction but do not severely impact their volume. As a result, the active part is formulated by:

$$F_a = (1 - \gamma) f_0 \otimes f_0 + \frac{1}{\sqrt{1 - \gamma}} (I - f_0 \otimes f_0) \quad (4)$$

The dynamics are characterized by an internal parameter γ that embodies the action potential and/or relevant ionic current. This parameter regulates the strength of active contraction; if this value is significant, there is substantial active contraction. When this value is zero, there is no active strain. The primary advantage of this "active strain" technique is that it implicitly preserves the ellipticity of the stress tensor while introducing only one new parameter into the model, making it a straightforward and effective methodology.

Figure 6:
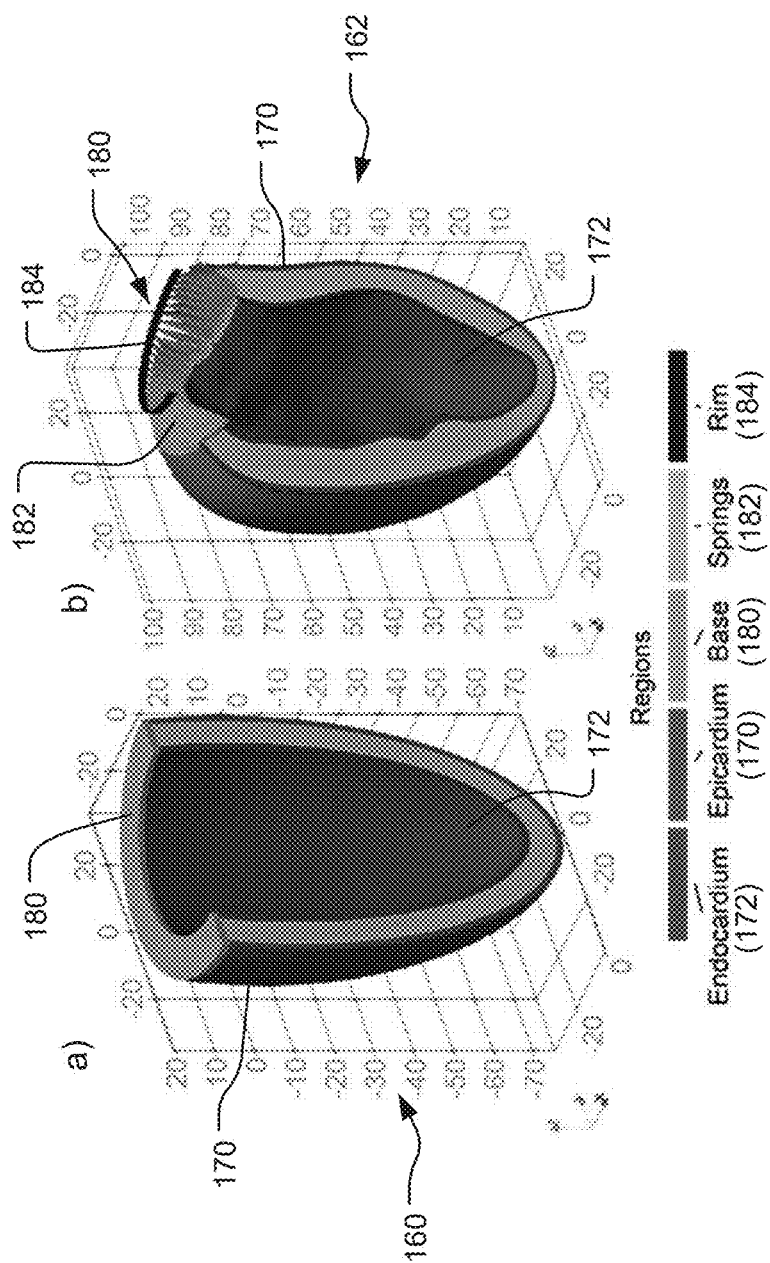
FIG. 6 illustrates boundary conditions for a) an idealized model and b) a patient-specific model.

With reference to FIGS. 5 and 6, two geometries were used in this study: an idealized truncated ellipsoid (LVIDEAL) 160 and an anatomic representation of an actual patient (LVPAT) 162. Both meshes were mainly composed of hexahedral elements. During preliminary testing, it was determined that the number of layers through transmural thickness directly influences the resultant deformation. Therefore, a mesh independence study was performed for each geometry, and converged mesh indicates that about at least six layers of quadratic elements or about at least eight layers of linear elements are preferred throughout the thickness. After performing a mesh convergence study, finite element (FE) models consisted of 16992 elements for the LVIDEAL 160 and 83648 elements for the LVPAT 162.

As shown in FIG. 5, the fiber orientation at the epicardium 170 is −60° and the fiber orientation at the endocardium 172 is +60° for each of the ideal geometry 160 (FIG. 5a) and the patient-specific geometry 162 (FIG. 5d). The uniform transmural variation along the myocardium wall is highlighted in FIG. 5b. An illustrative angle measurement is show in FIG. 5c, in which $e_c$ and $e_L$ are the circumferential and longitudinal directions, respectively, and α is the angle describing the $f_0$ vector (this angle is in-plane with $e_c$ and $e_L$ axes).

Moreover, recognizing that our constitutive model is heavily dependent on defined fiber orientations, we applied a rule-base reconstruction algorithm (e.g., a custom MATLAB code) which can create the fiber field from defined boundaries (endocardial and epicardium orientations) while being adaptable to various geometries. This approach is also used in the field when clinical DT-MRI data are unavailable. As can be seen in FIGS. 5 a) and b), the muscle fiber orientations change linearly with the position through the wall: from a negative angle ($α_{epi}$) on the epicardial surface 170 to nearly 0° in the mid-wall to a positive angle ($α_{endo}$) on the endocardial surface 172. Homogeneous distribution of the fiber angle was assumed over the entire myocardium 174.

FIG. 6 illustrates two approaches for boundary conditions. The first is a simple fixed base 180 for the idealized geometry 160 and the second is a spring-constrained strategy for the non-idealized (e.g., patient-specific) case 162. For the idealized geometry 160, we fixed the base 180 nodes in the z coordinate (longitudinal direction), which prevents the mesh from any rigid motion as forces along the x and y directions equilibrate due to the axisymmetric in the geometry. For the LVPAT 162, we constrained the basal region 180 with virtual springs 182 having a spring constant (e.g., a spring constant of 0.1 N/mm) attached to a fixed rim 184, mimicking the tethering effect of peripheral tissues. This method permitted movement along all directions, but restricted rigid body motion, which closely resembles physiological constraints. The pressure load is applied uniformly on the endocardial 172 surface for both cases.

Figure 7:
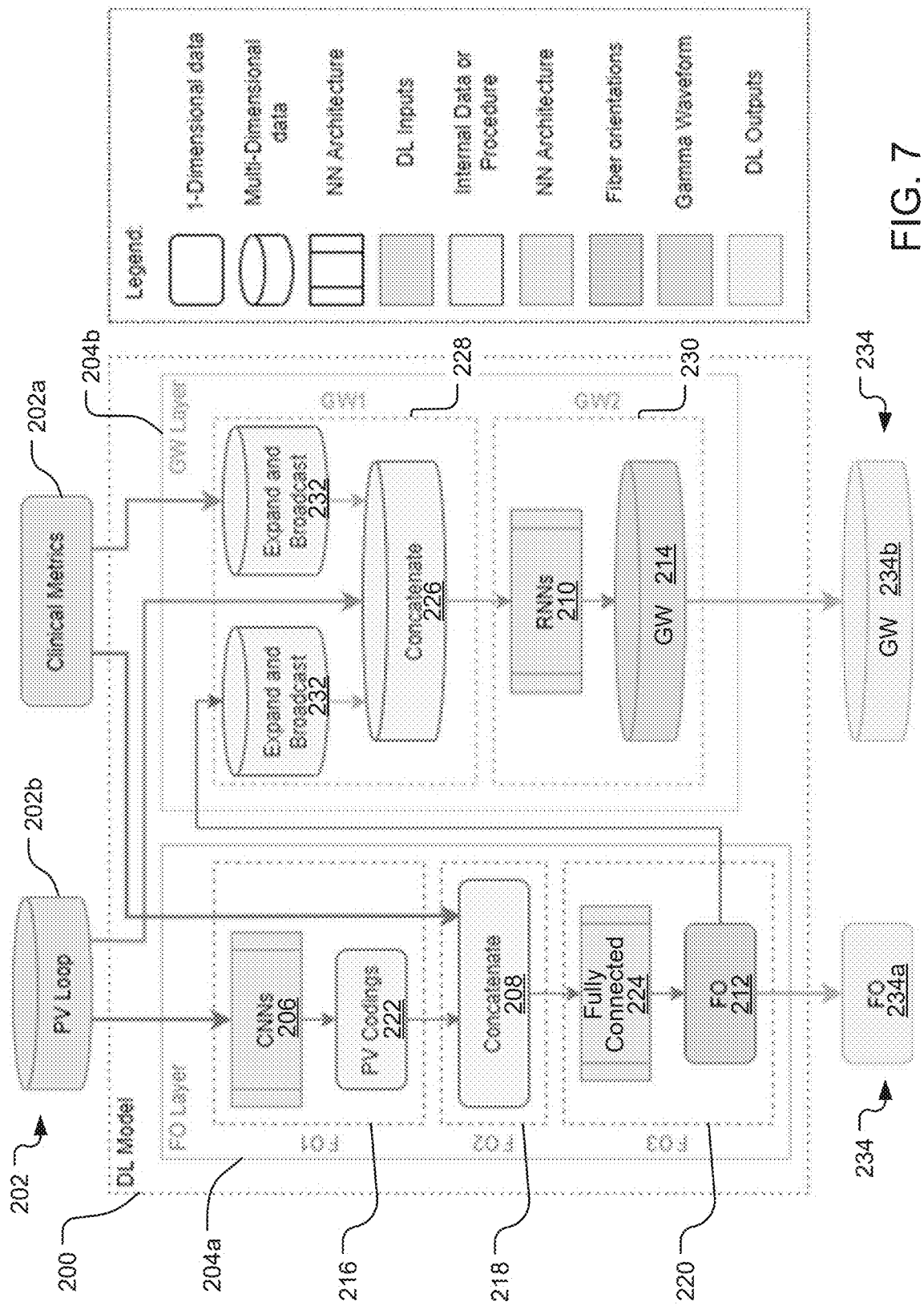
FIG. 7 is a schematic illustration of a deep learning model according to an embodiment of the disclosure.

FIG. 7 illustrates a schematic diagram of an example deep learning model 200 according to an embodiment of the present disclosure. Our deep learning model 200 can include two main goals: the first is to construct a gamma, γ waveform that accurately captures the active contraction behavior of patient-specific data during a cardiac cycle, while the second is to estimate the fiber angles, $α_{epi}$ and $α_{endo}$, at endocardium and epicardium. As inputs 202 for our model, we considered a set of six clinical metrics (CMs) 202a that can be easily extracted from medical imaging modalities. These clinical metrics can include longitudinal shortening (LS), radial shortening (RS), wall thickness (WT), longitudinal strain (LST), circumferential strain (CST), and ejection fraction (EF). Other inputs 202 can include ejection fraction, apex torsion, or other representations of the cardiac cycle through pressure-volume (PV) loops 202b. The clinical metrics are described in further detail below with reference to FIG. 24.

In one example our deep learning model comprises two functional components 204a, 204b: one that outputs the set of fiber orientations (FO) 234a and another that generates the gamma waveform (GW) 234b. The first component (FO layer) 204a is composed of a convolutional neural network (CNN) encoder 206 that extracts pertinent information from the input PV loop 202b; this data is then concatenated 208 with the input CMs 202a data and passed through a specialized network formed by fully connected layers and skip connections to estimate fiber orientations, as shown in FIG. 7. The second component (GW layer) 204b is mainly composed of a recurrent neural network (RNN) 210 that combines the PV loop 202b, clinical metrics 202a, and fiber orientation 212 to estimate a gamma waveform 214.

The FO layer 204a is composed of three stages: (1) Extract integral features from the PV loop 202b (see 216), (2) combine them with the clinical metrics input 202a (see 218), and (3) estimate the fiber orientations 212 (see 220). The first stage 216 treats the PV loop 202b as a static signal with two channels (pressure and volume) and reduces the data dimension by employing a series of CNNs 206 in conjunction with maximum pooling layers. This results in the retrieval of a 1D set of relevant "PV codes" 222 that represent key characteristics of the given PV loop 202b. This part of the network may be trained separately as an autoencoder, in which generated PV codes are used to reconstruct the original PV loop, ensuring a significant relationship between codes and the PV loop. The second stage 218 of the FO layers 204a concatenates 208 these codes with the 1D set of clinical metrics 202a. The third and last stage 220 takes the concatenated information 208 and employs a succession of fully connected layers 224 with, for instance, local skip connections at every two layers and general skip connections to the initial information at every five layers to generate the set of fiber orientations. This example architecture is further explained below.

The GW 204b layer is, in some embodiments, a straightforward two-step process: (1) Concatenate 226 the PV loop 202b with clinical metrics 202a and fiber orientations 212 from the FO layer 204a (see 228), and (2) employ an RNN architecture 210 to retrieve the gamma waveform 214 as a time-distributed sequence (see 230). The first step 228 is achieved by expanding dimensions and broadcasting 1D inputs 232 (fiber orientations 212 and clinical metrics 202a) to match the length of the given PV loop 202b. The result is a single (n×m) stream of data, in which n is equal to 4 (representing pressure, volume, and fiber orientations at endocardium and epicardium) plus the number of clinical metrics 202a and m is the length of the PV loop 202b. This data is then utilized as inputs for the RNN architecture 210, which, in some embodiments, considers the temporal relationship within the PV loop 202b and uses the supplementary information to hypothesize a time-varying gamma waveform 214 based on the given cardiac cycle and patient-specific data.

Our example deep learning model 200 focused on identifying the fiber orientations 234a on the endocardium and epicardium, as well as on inferring a gamma waveform 234b that effectively depicts the active contraction behavior of a patient-specific myocardium throughout a cardiac cycle. Thus, for a training procedure to be more effective, the dataset should be represented as a multidimensional parameter space that links inputs 202, clinical metrics 202a, and pressure-volume values 202b to our outputs 234, fiber orientation values 234a, and gamma waveform 234b.

The dataset may be obtained via a variety of methods. One exemplary method is to use data gathered directly from a clinical environment. However, while clinical measures and PV loops would be factual, it can be cumbersome to tie them to an internal constitutive model parameter gamma. A second exemplary method is synthesizing our dataset by extracting results from various Finite Element (FE) simulations. This option may entail two strategies: (a) a greedy search and (b) a systematic approach. The first strategy is commonly found in the literature; wherein random parameters are used as inputs for FE simulations. Although this strategy is plausible, due to constraints imposed by randomized parameter search, it typically requires thousands of simulations to cover a wide range of anticipated results and often leads to feature imbalance. Thus, a preferable method, as further described below with reference to FIG. 10, can include the following two main components: (i) a lumped-parameter model to generate a broad spectrum of physiological and pathological PV loops (see, for example, FIG. 8) and (ii) two machine learning models pre-trained on the time-independent dataset of geometric characteristics to estimate clinical metrics.

In some embodiments, a lumped parameter model can be used (e.g., a CVSim lumped-parameter model). Such software can create a variety of cardiac responses using a lumped-parameter model of the human circulatory system (see, for example, FIG. 8a) that was created and has been used for research and teaching quantitative physiology. Random physiological values (within valid ranges) can be used as inputs for CVSim, and an exemplary PV loops were recorded. These were normalized and used as input parameters for the PV generator function. This PV generator function expanded the available dataset by randomly translating, scaling, or descaling a random PV loop from the available PV loops recorded with CVSim. Lastly, to maintain the PV loop valid for any, for instance, left ventricular model, we ensured that each PV loop had the same initial and maximum volume; in addition, pressure values were capped (if necessary) to valid physiological ranges.

Figure 9:
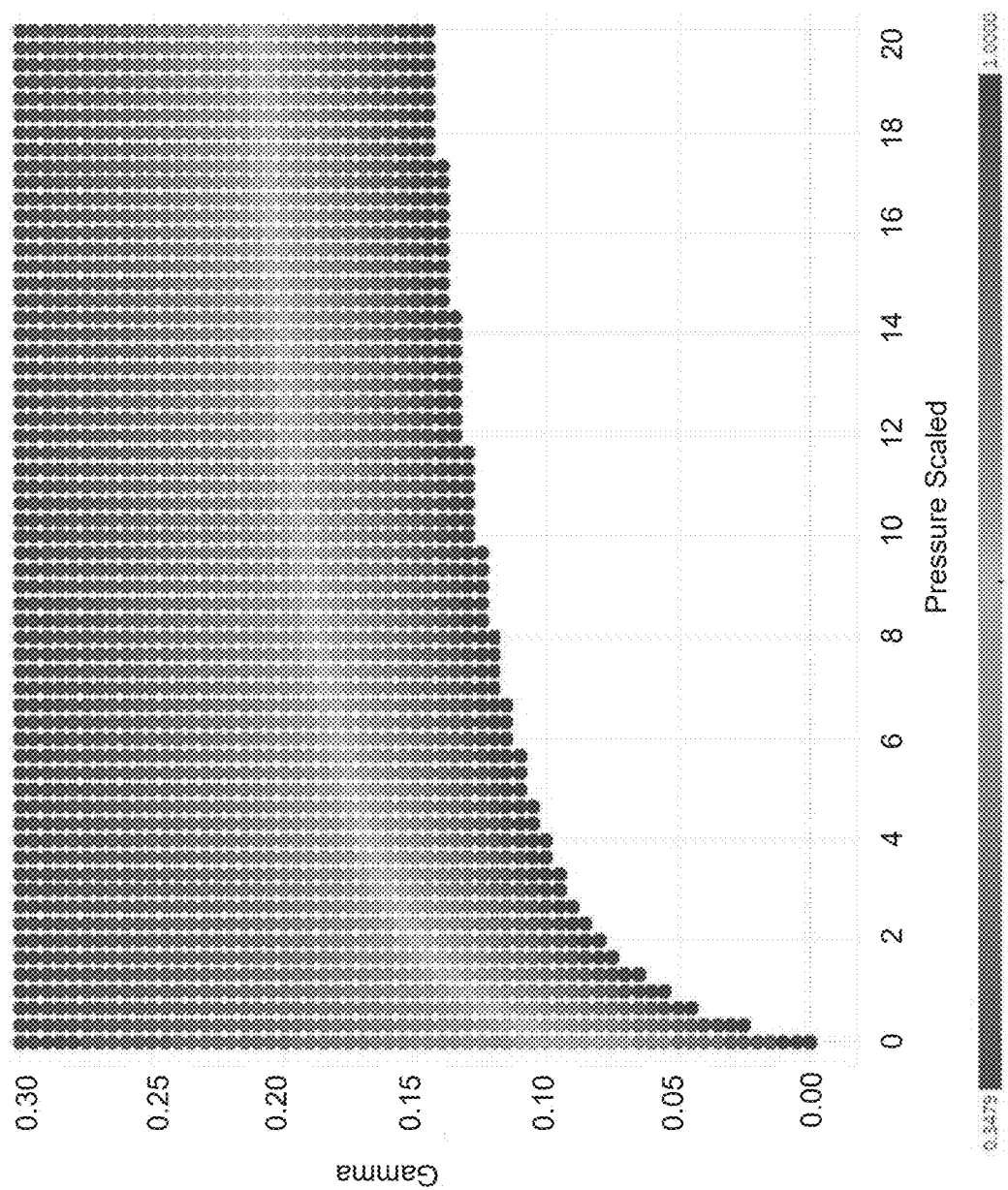
FIG. 9 is an exemplary finite element imploration to estimate clinical metrics and a gamma waveform that can be used to train regressors.

For the second component of the preferred method, we developed two distinct, fully connected dense regressors: (a) a geometric characteristics (GC) model, which is directed to estimate geometric characteristics of the left ventricle (LV), and (b) the gamma (GR) model, designed to estimate individual gamma. Both models accept a P-V (pressure-volume) value and a set of fiber orientations as inputs. Further, the training data for the regressors were obtained from FE simulations with variant $\gamma$ value (0–0.3) and fiber orientations (from approximately −40 to −80 degrees at endocardium and approximately 40 to 80 degrees at epicardium) using linearly increasing pressure loads from 0 to 20 kPa (see, for example, FIG. 9). We recorded the corresponding cavity volume and geometric characteristics, such as longitudinal and circumferential length, wall thickness, apex-basal distance, and inner radius, from the deformed myocardium for each pressure value.

As each step in a FE simulation can be considered the result of static equilibrium, we can correlate the specified step values (pressure, volume, gamma, and fiber orientations) with the corresponding geometry. As a result, this approach advantageously allows a systematic variation of desired model parameters, enabling us to not only fine-tune each parameter's step size, but also eliminate the need to account for any time-dependent relationships. Subsequently, our strategy significantly reduced the number of FE simulations necessary to produce a suitable dataset for our final model: we were able to generate over 220,000 synthetic valid data entries using less than 1100 FE simulations. The traditional method of extracting training data directly from FE simulations would take significantly more time and memory.

Figure 8:
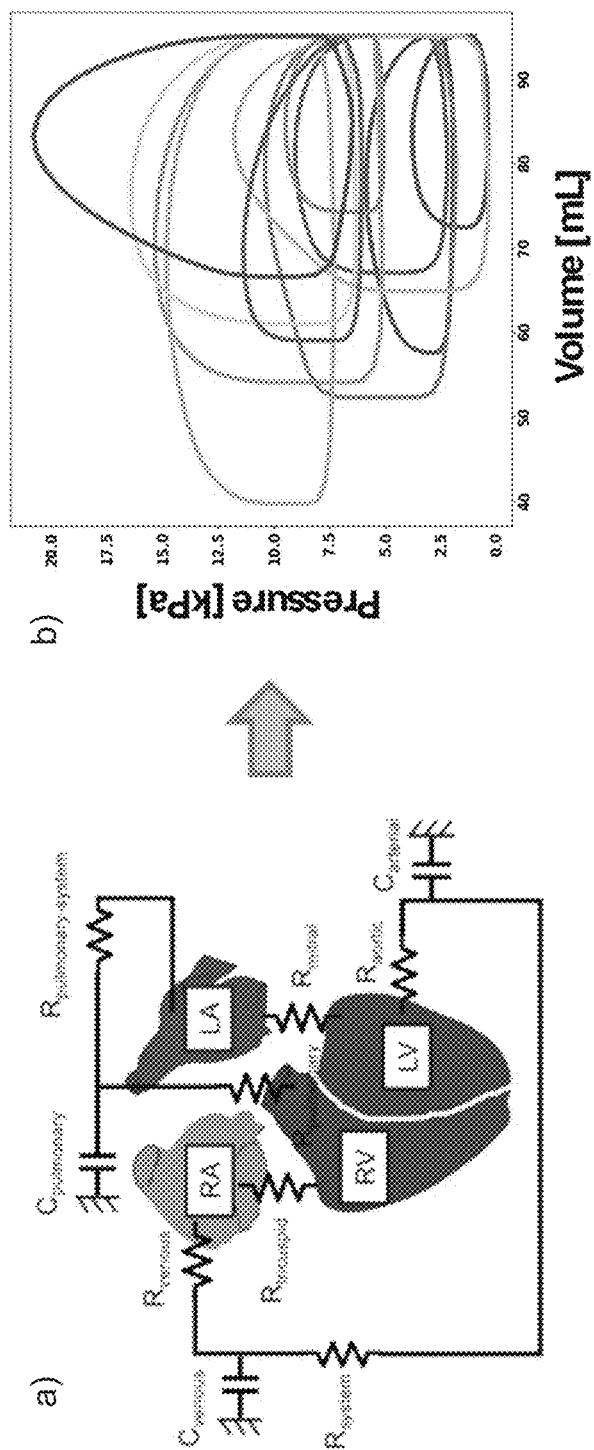
FIG. 8 is an exemplary lumped parameter model that can be used to generate PV loops; a) illustrates a schematic diagram of the lumped parameter model and b) illustrates exemplary PV loops.
Figure 10:
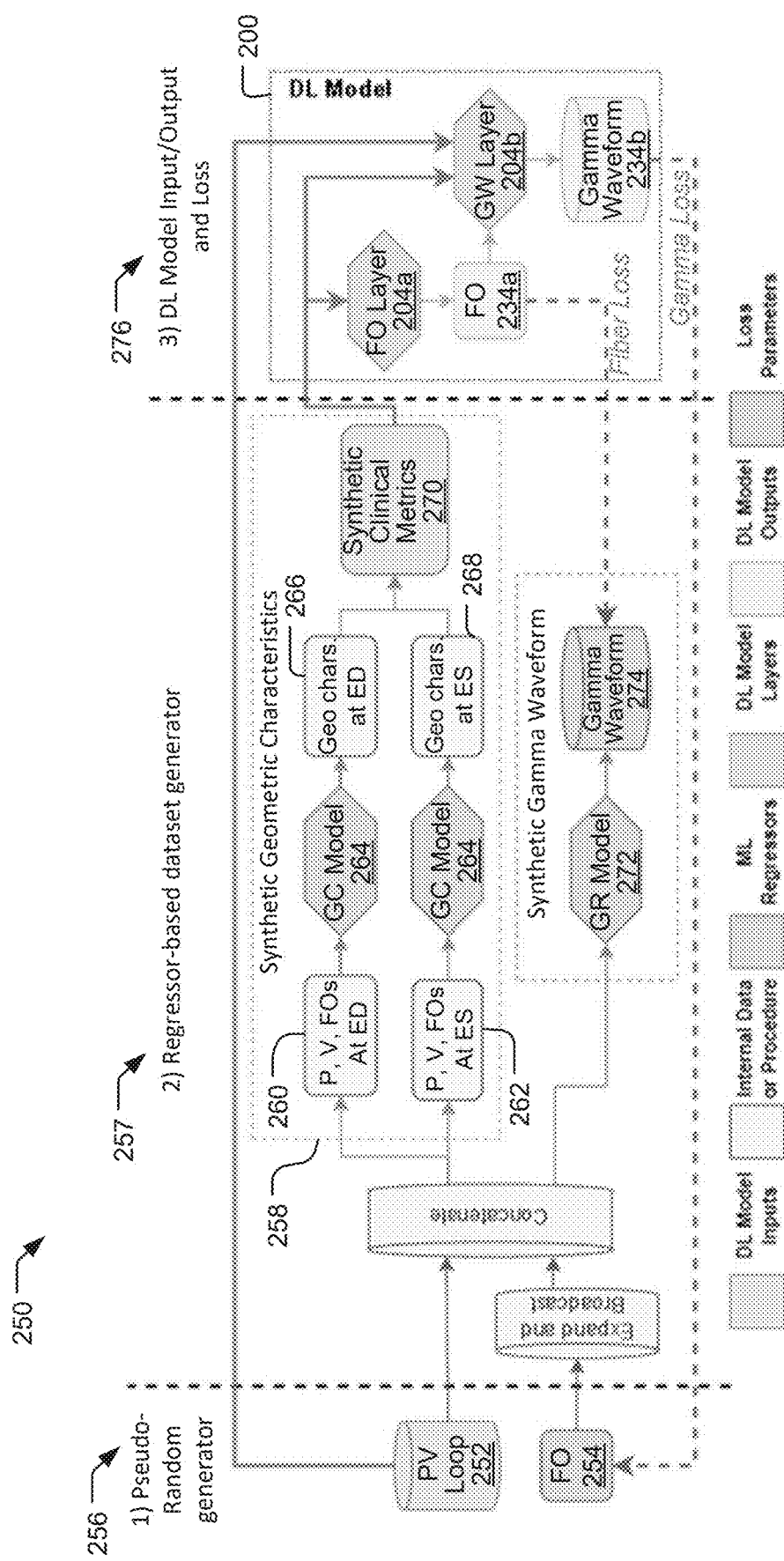
FIG. 10 is a schematic illustration of a method for data generation for training, validating, and testing a deep learning model.

With reference to FIG. 10, a schematic diagram 250 according to an embodiment of the present disclosure is shown. The diagram 250 represents an example method and illustrates the schematics of data generation for training, validating, and testing a deep learning model, such as the model 200. As shown in FIG. 8, PV loops 252 and fiber orientations 254 are generated in a pseudo-random fashion at the start 256 of training. Next, at 257, using pre-trained regressors, synthetic data is generated 258. End-diastolic (ED) 260 and end-systole (ES) 262 pressure and volume values are respectively coupled with fiber orientations and sent into the GC model 264 (e.g., a first intermediate model), producing their respective geometric characteristics 266, 268; these are then utilized to formulate synthetic clinical metrics 270. Simultaneously (or optionally in series or in parallel, parallel such that the models are run during an overlapping time period), the PV loop's 252 pressure and volume values are combined with the fiber orientations 254 and inputted to the GR model 272 (e.g., a second intermediate model), which generates a synthetic gamma waveform 274. Finally, the PV loop 252 and synthetic clinical metrics 270 are supplied to the DL model 200, which re-assigns them to the appropriate data flow. The estimated fiber orientations 234a from the FO layer 204a are produced within the DL model 200 and utilized as one of the inputs to the GW 204b layer and one of the DL model's 200 outputs 234. Finally, the DL model 200 outputs the estimated gamma waveform 234b based on the PV loop 202b, clinical measures 202a, and estimated fiber orientations 234a. At 276, the model's mean squared error (MSE) loss is computed using the estimated fiber orientations 234a and gamma waveforms 234b and is compared to their respective synthetic values from the dataset generators.

Figure 11:
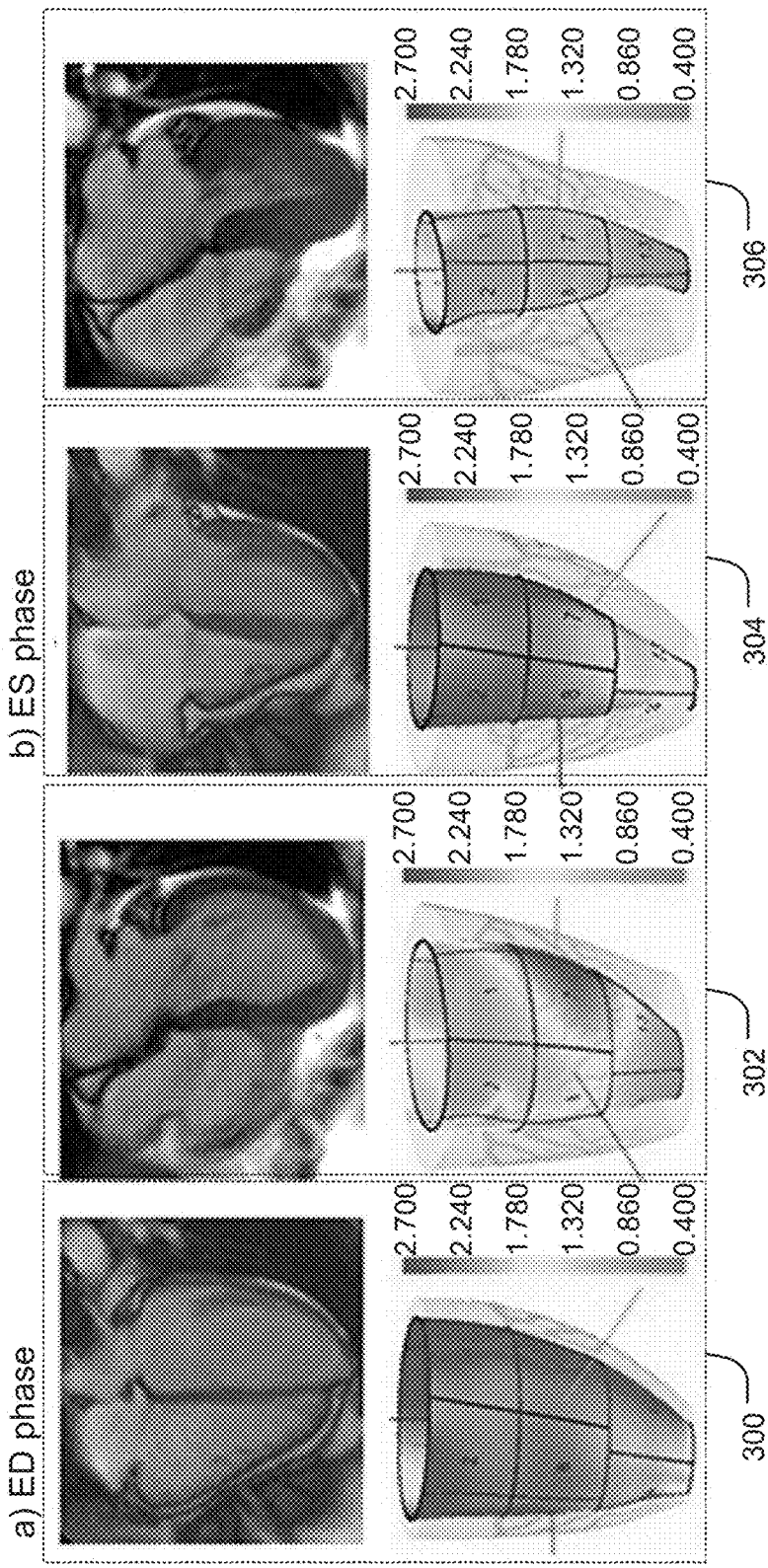
FIG. 11 shows an example of a constitutive model being applied on a normal subject and a diseased subject; a) illustrates the model in an end-diastolic phase and b) shows the model in an end-systolic phase.

FIG. 11 illustrates an example of a constitutive model being applied on a normal subject and a diseased subject in each of an end-diastolic phase and an end-systolic phase. In particular, FIG. 11a shows a normal subject 300 in an end-diastolic phase and a diseased subject 302 in an end-diastolic phase. FIG. 11b shows a normal subject 304 in an end-systolic phase and a diseased subject 306 in an end-systolic phase. The model provides a stress distribution along respective endocardium walls for each of the subjects and scenarios. The variations in stress distributions can help physicians identify possible causes for various diseases.

Figure 12:
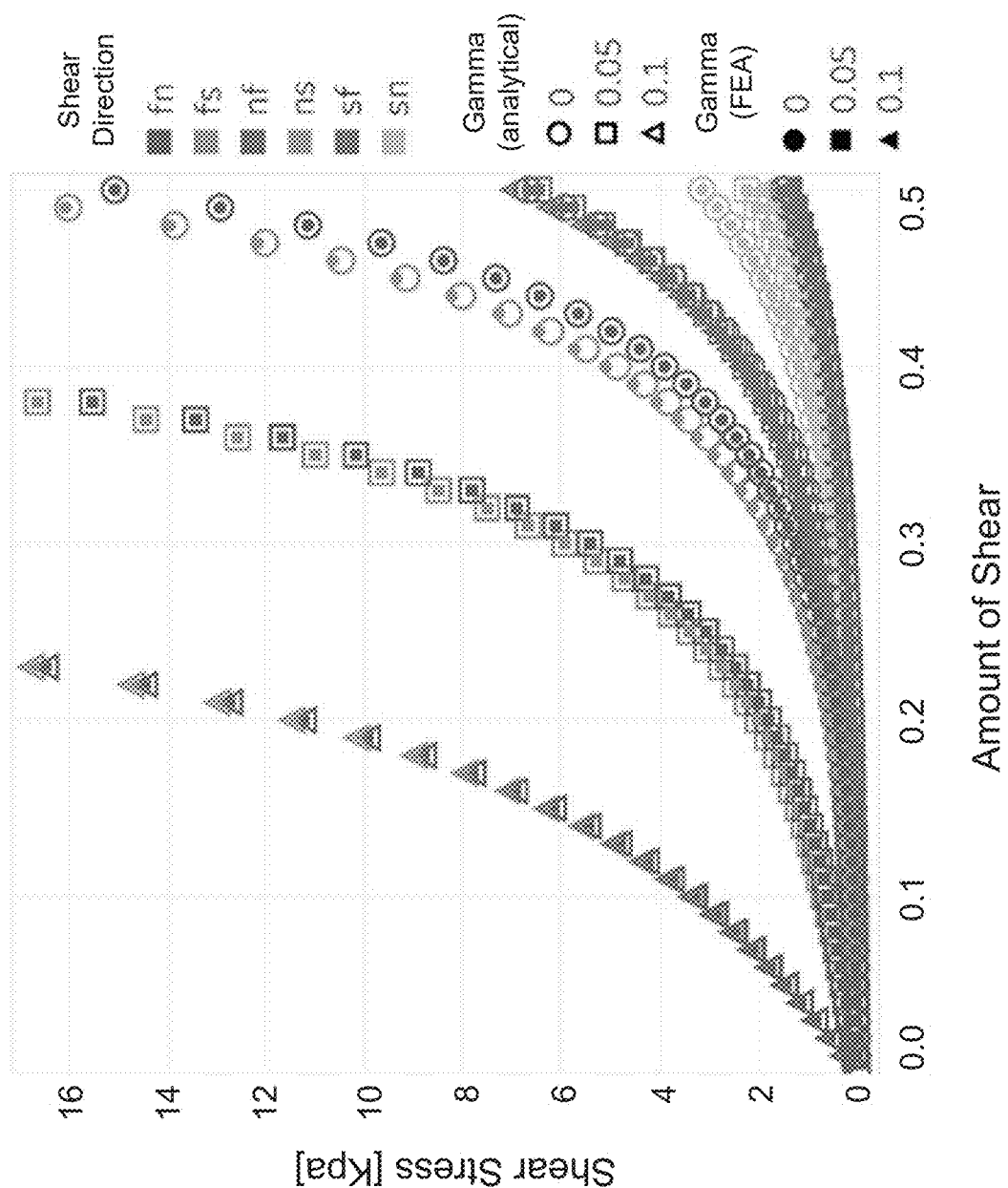
FIG. 12 illustrates a graphical comparison between finite element results and analytical solutions.

In some implementations, a constitutive model according to embodiments of the present disclosure, can be implemented in, for instance, an FEBio software through custom plugins. The assessment of our passive model implementation included comparing the results of FE simulations to analytical solutions of a cube element under shear. Six cyclic simple shear tests were conducted. Each test included clamping one side of a 1 mm cube and shearing the opposing side in the fs, fn, sf, sn, nf, and ns directions. The comparison between the FE results and analytical solutions is shown in FIG. 12. As can be observed, the stress-shear relationships calculated via FEA are well aligned with their analytical solutions, indicating that our implementation is legitimate.

Our active model implementation was evaluated similarly to the passive model: we extended the analytical solutions to include the active counterpart and compared them with FE results. Results for different values of γ are shown in FIG. 12, indicated by square and triangle shapes. As anticipated, the material exhibits a stiffer behavior when stretched along the fiber directions (fn and fs) with an increasing γ value, reflecting the behavior of active contraction.

The assessment of our deep learning model may be divided into two aspects: (a) a comparison of model predictions and expected values from training, validating, and testing datasets, and (b) a comparison of FE simulations produced with inputs from our model and anticipated results (treated as ground truth).

The first part of our model's evaluation is provided in Table 2, which shows the mean absolute error (MAE) between predicted values and 'actual' values from training, validating, and testing datasets, respectively, for both the GC and GR regressors and our final DL model. Each dataset was kept separate throughout the study, and the testing dataset was used only after each model was trained. As shown, the two regressors obtained significantly low MAE without overfitting trends, making them suitable for producing the dataset for the final model. Moreover, our final DL model achieved a MAE of less than one degree for fiber orientations and markedly low error for gamma values. Additionally, our model did not exhibit overfitting during training, allowing for a broader generalization of the data on which it was trained.

the peak gamma value for both idealized and patient-specific models, confirming the relationship: as volume decreases, active contraction should increase. ESV also has a strong correlation ($0.8 <= r < 1.0$) with half peak width (HPW) of the gamma waveform. In addition, a positive and very strong correlation ($0.8 <= r < 1.0$) is discovered between peak gamma and Ejection Fraction (EF) and Stroke Volume (SV). Interestingly, Stroke Work (SW) has a weak ($0.2 <= r < 0.4$) to moderate ($0.4 <= r < 0.6$) association with gamma values. In addition, peak pressure does not have a direct correlation ($|r| <= 0.2$) with gamma values, as other factors might compensate for the contraction as pressure increases. Lastly, it is noticeable that all clinical metrics, apart from longitudinal strain and longitudinal shortening, have strong correlations with peak gamma values.

Conversely, it is discernible that PV loops do not directly affect endocardial and epicardial fiber angles. This is mainly a result of our uniform distribution over sampling values for fiber orientations in our dataset, which covered values from +/−40 to +/−80 degrees in both orientations. Notably, our model was trained to identify a gamma waveform for each combination of fiber angles on distinct PV loops and clinical measures. This prompted the model to determine an optimal solution independent of the combination of fiber orientations.

The second aspect of evaluation was to conduct a thorough analysis of the study, which included running FE simulations using the DL model's output and comparing the results to 'true'/anticipated values taken from the sampling dataset. This procedure was as follows: (1) randomly choose a sample of a new sampling dataset, (2) feed the DL model

TABLE 2

Mean absolute error for all models from training, validating, and testing datasets.

| Geometry | Model | Component | Training Dataset | | Validating Dataset | | Testing Dataset | |
|---|---|---|---|---|---|---|---|---|
| | | | MAE | # Samples | MAE | # Samples | MAE | # Samples |
| Ideal | GC | Geometric Metrics | 7.326e−04 | 5.815e5 | 6.154e−04 | 2.326e5 | 6.151e−04 | 1.55e5 |
| | GR | γ values | 0.0012 | 5.815e5 | 7.560e−04 | 2.326e5 | 7.529e−04 | 1.55e5 |
| | DL | Fiber orientation | 3.566 | 52800 | 2.421 | 28800 | 2.446 | 14400 |
| | | γ waveform | 0.0020 | 52800 | 0.0019 | 28800 | 0.0018 | 14400 |
| PAT | GC | Geometric Metrics | 8.206e−04 | 5.815e5 | 7.078e−4 | 2.326e5 | 7.088e−4 | 1.55e5 |
| | GR | γ values | 0.0026 | 5.815e5 | 0.0020 | 2.326e5 | 0.0019 | 1.55e5 |
| | DL | Fiber orientation | 3.1774 | 52800 | 2.852 | 28800 | 2.850 | 14400 |
| | | γ waveform | 0.0020 | 52800 | 0.0019 | 28800 | 0.0019 | 14400 |

Figure 13:
FIG. 13 shows a correlation matrix between inputs and outputs for a) an idealized scenario and b) a patient-specific scenario.

Moreover, to better understand and evaluate the deep learning model, FIG. 13 shows the correlation matrix between inputs and outputs for a) idealized and b) patient-specific scenarios. PV loop inputs were broken down into distinct features that effectively describe their characteristics for the computation of the correlation matrix. These features include end-diastole pressure (EDP), end-systole pressure (ESP), coupling ratio (CR, expressed as SV/ESV), arterial elastance (Ea, expressed as ESP/SV), end-systole elastance (Ees, expressed as ESP/ESV), stroke volume (SV, expressed as EDV-ESV), stroke work (SW, expressed as the area enclosed by the PV loop), and peak pressure (Pmax). In addition, we included the half-peak width (HPW) of the gamma waveform for additional analysis.

The results indicate a strong negative correlation ($-1 <= r < -0.8$) between the End-Systolic Volume (ESV) and with the PV loop and synthetic clinical measurements, (3) run the FE simulations with the parameters from the DL model output, and (4) assess the FE output in contrast to the chosen dataset sample. This procedure was done for both ideal and patient-specific geometries. The sampling dataset was created similarly to the testing dataset; however, we limited the PV loops to a normal distribution for ejection fraction values centered at 45%, roughly achieving equal sample sizes for healthy and diseased patients.

Figure 14:
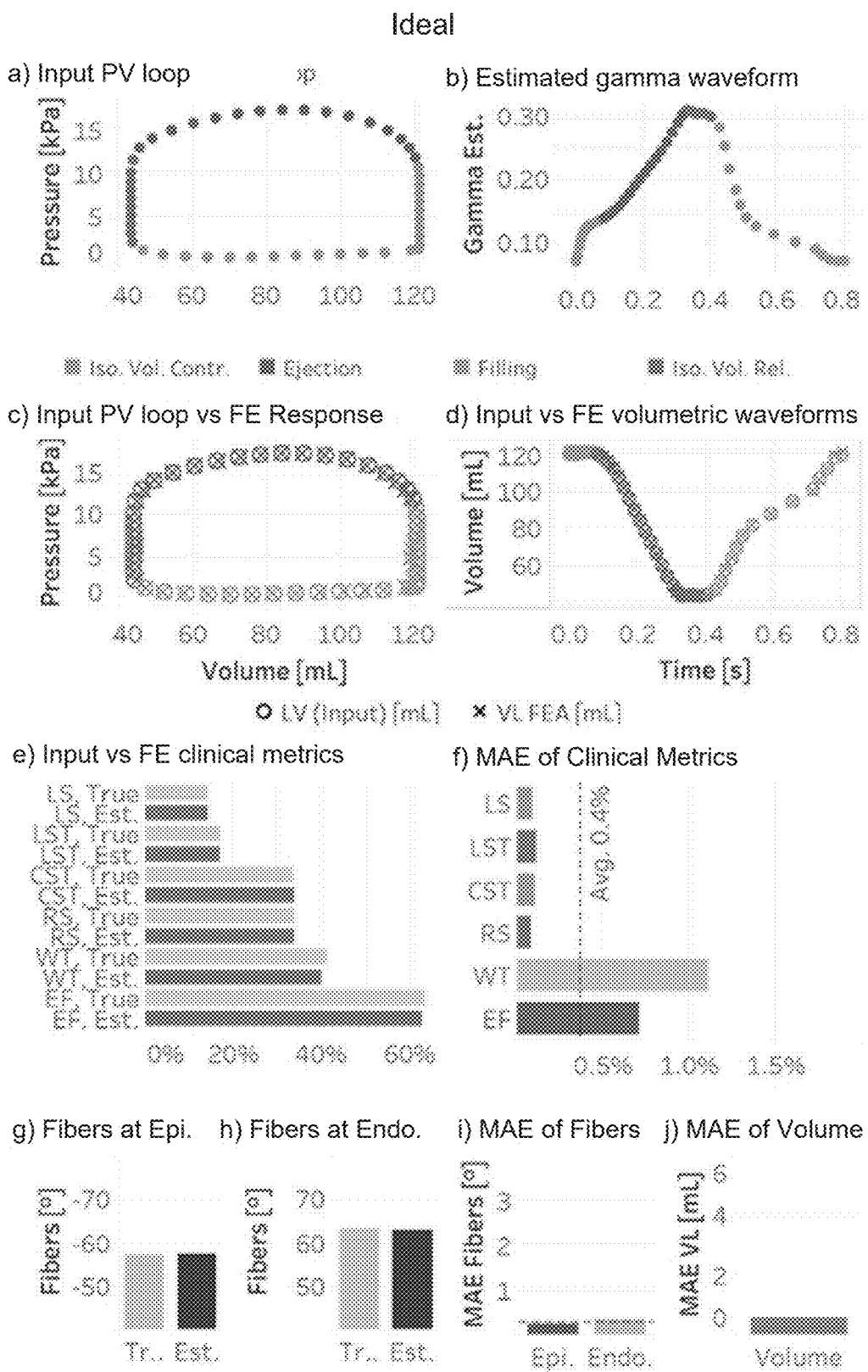
FIG. 14 is a representative sample evaluation study for ideal simulations; a) represents the input PV loop, b) depicts the estimated gamma waveform from a deep learning model, c) illustrates the PV loop comparison of true values and predicted values from a finite element simulation, d) shows a volume waveform comparison of true values and predicted values from the finite element simulation, e) represents the inputs of clinical metrics, f) shows the mean absolute error (MAE) for each clinical metric, g) illustrates the true and predicted fiber orientations for the epicardium, h) illustrates the true and predicted fiber orientations for the endocardium, i) represents the MAE for fiber orientation at epicardium and endocardium, and j) shows the MAE for the volume waveform.
Figure 15:
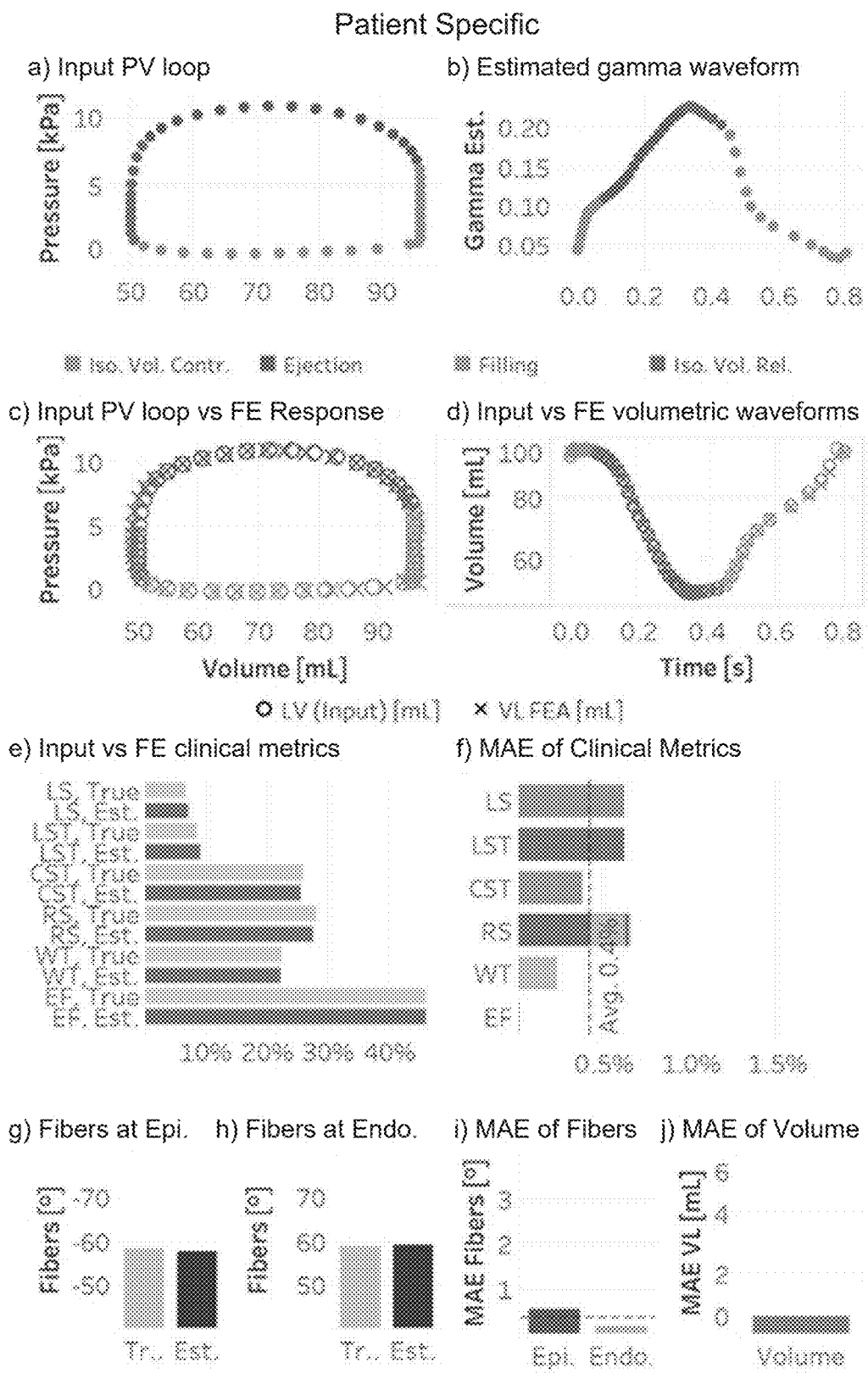
FIG. 15 is similar to FIG. 14 and is a representative sample evaluation study for patient-specific simulations; a) represents the input PV loop, b) depicts the estimated gamma waveform from a deep learning model, c) illustrates the PV loop comparison of true values and predicted values from a finite element simulation, d) shows a volume waveform comparison of true values and predicted values from the finite element simulation, e) represents the inputs of clinical metrics, f) shows the mean absolute error (MAE) for each clinical metric, g) illustrates the true and predicted fiber orientations for the epicardium, h) illustrates the true and predicted fiber orientations for the endocardium, i) represents the MAE for fiber orientation at epicardium and endocardium, and j) shows the MAE for the volume waveform.

A representative evaluation of this process for the idealized (I) and patient-specific (II) cases are illustrated in FIGS. 14 and 15, respectively. An input PV loop is shown in FIGS. 14a and 15a and the clinical metrics input are shown in FIGS. 14e and 15e. The DL model's prediction of fiber orientations are shown in FIGS. 14g, 14h, 15g, and 15h, and the gamma waveforms are shown in FIGS. 14b and 15b.

Next, the comparison of input and obtained PV loops from the FE simulation are shown in FIGS. 14c and 15c, while specific volume waveforms (true and obtained) are shown in FIGS. 14d and 15d. The comparison between clinical metrics from the DL model's input and the FE simulation is shown in FIGS. 14e and 15e. Finally, the mean absolute errors for critical quantities of the prediction are illustrated in FIGS. 14f, 14i, 14j, 15f, 15i, and 15j. All predictions agree closely to their anticipated values.

As observed, the predicted gamma waveform is at its maximum around the end of systole, displaying the most vigorous contraction, and then decreases to about zero at the end of diastole. Regarding volume waveform, both ideal and patient-specific simulations yielded near-perfect solutions, with FE findings closely matching the volume waveform of the input PV loop. Moreover, all values for clinical metrics had a mean absolute error of less than 2%, with an average value of around 0.5%, indicating that simulations closely followed the expected deformations. Lastly, the predicted fiber orientation clearly reflects the anticipated orientation, with minor errors for both geometries. Overall, the findings demonstrate that the FE simulations based on predicted material parameters from the DL model closely matched the expected deformation over the entire cardiac cycle in both idealized and patient-specific scenarios.

Figure 16:
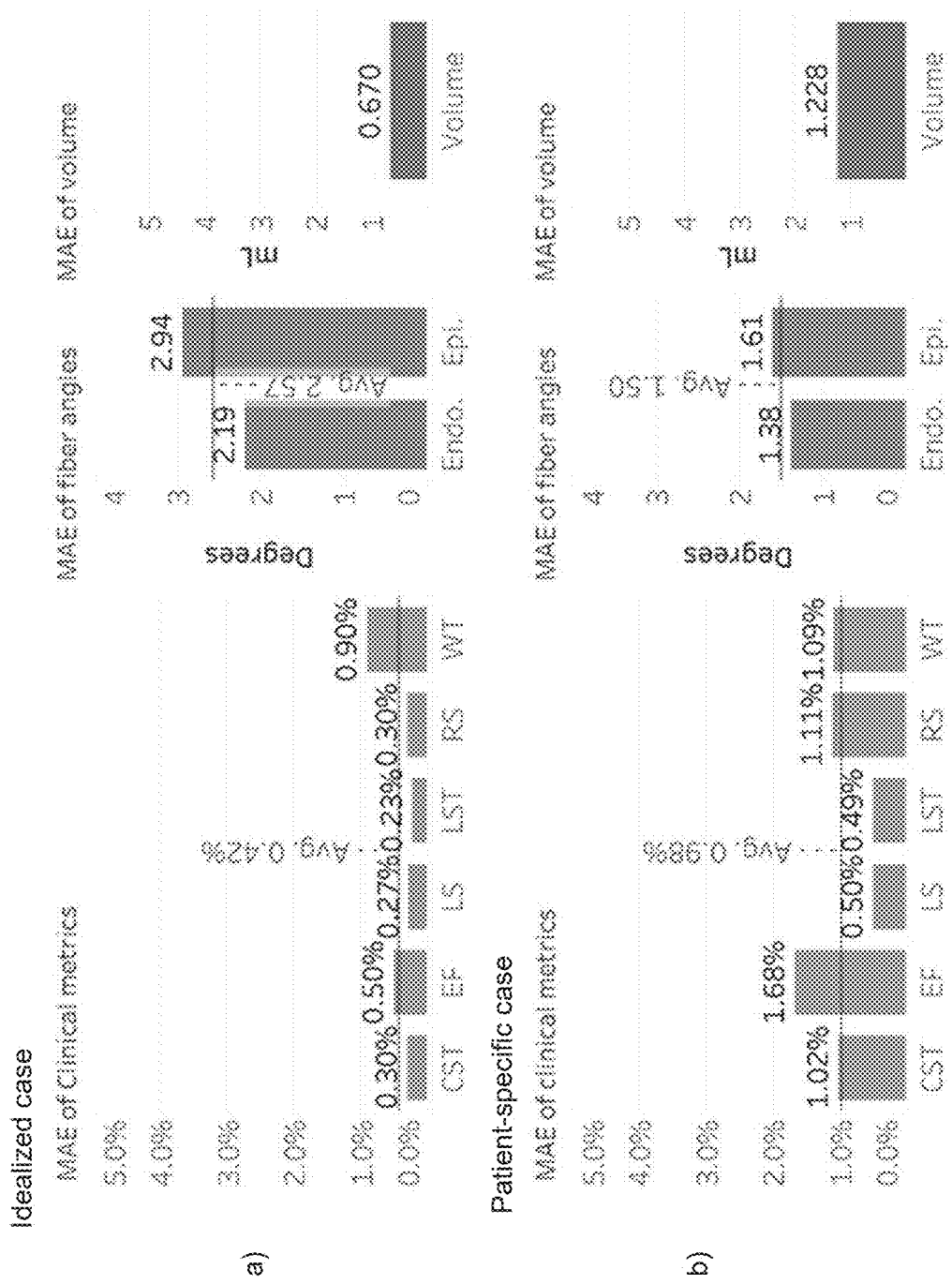
FIG. 16 is an exemplary overall study evaluation based on comparing finite element results and true values for a) ideal and b) patient-specific cases.

Further, for each evaluation of the sample dataset, we compared the mean absolute errors (MAE) between anticipated and predicted values for each clinical metric, fiber orientation, and volume waveform. The results for the ideal case are shown in FIG. 16a, while results for the patient-specific case are illustrated in FIG. 16b. Clinical metrics and volume have significantly low MAEs, indicating an accurate prediction of FE model parameters from the DL model over the whole cardiac cycle; nevertheless, fiber angles have a slightly higher MAE, yet their average is still below 5% of their maximum range.

Figure 17:
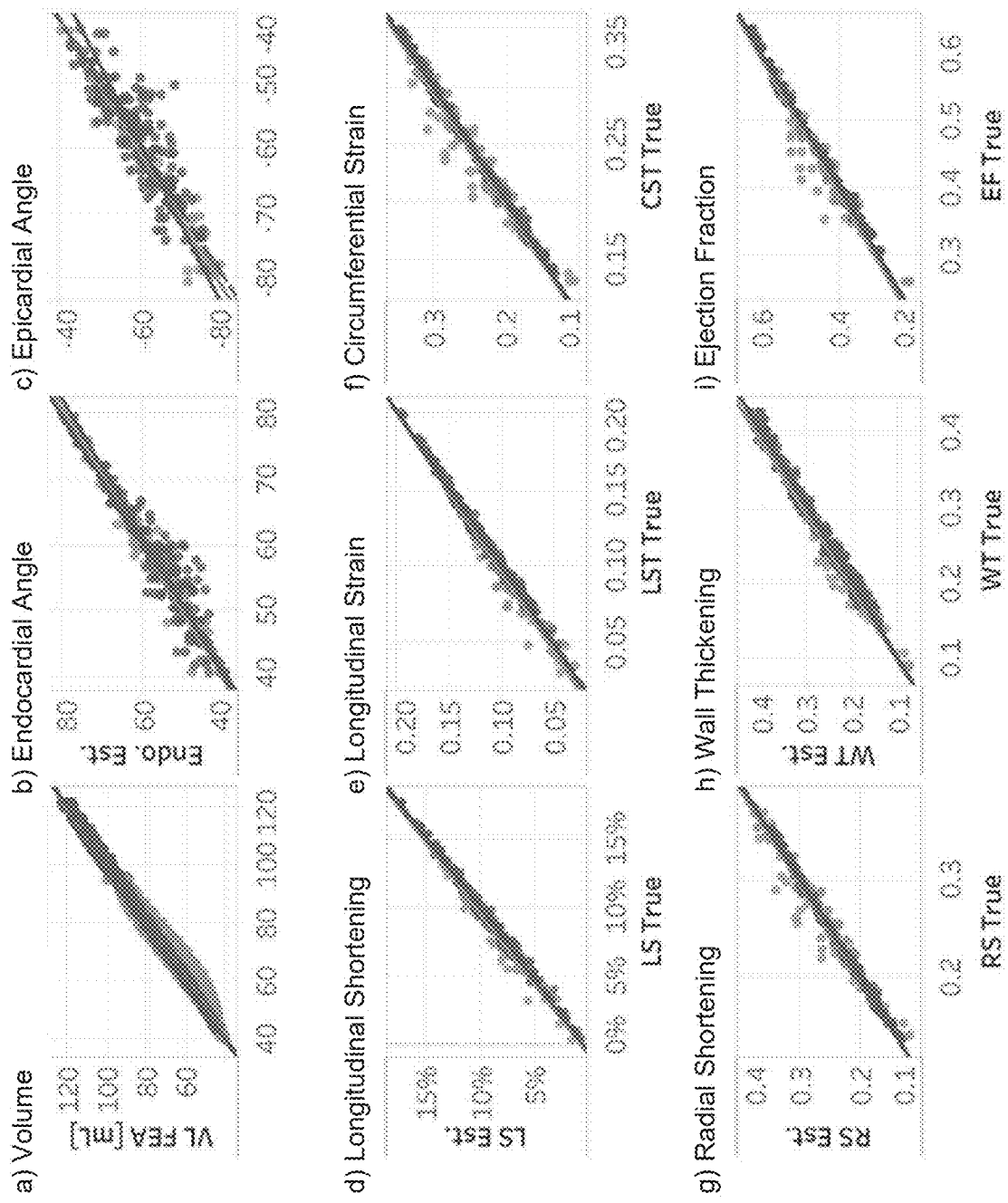
FIG. 17 illustrates accuracy plots for 200 samples from the idealized (blue) and patient specific (orange) study evaluation; trend lines are shown to illustrate the overall accuracy; subplots illustrate values for a) volume, b) endocardial angle, c) epicardial angle, d) longitudinal shortening, e) longitudinal strain, f) circumferential strain, g) radial shortening, h) wall thickening, and j) ejection fraction.

FIG. 17 illustrates the aggregation of sample results from this study's examination for both idealized and non-idealized scenarios. Each density plot in FIG. 17 represents our study's accuracy, with the y-axis depicting values extracted from FEA simulations and the x-axis portraying the respective 'true' values. Markers in blue represents the ideal case, while markers in orange refer to the patient-specific case. In addition, trend lines are shown. Most predicted values overlap with their respective 'true' values, showing a diagonal trend line (best-case scenario). Errors are slightly more prominent in the patient-specific scenario, possibly due to the increased complexity of non-idealized geometry that can affect numerical computations of clinical metrics. On the other hand, the largest deviation occurs for endocardial and epicardial angles. Based on accuracy plots and the overall MAE (see FIG. 16), it is noticeable that these errors are more extensive for the idealized case. Considering that the simulation followed the expected deformation because both volume and clinical metric errors were significantly low, the larger errors in fiber orientation may reflect that multiple solutions for these values may satisfy the required conditions when a simplified geometry is considered.

Our research included a component to explore the relationship between constitutive modeling and clinical assessments. In this part, we illustrate the outcomes of our model while examining important clinical indicators using results obtained from our evaluation study as well as designated testing datasets.

Figure 18:
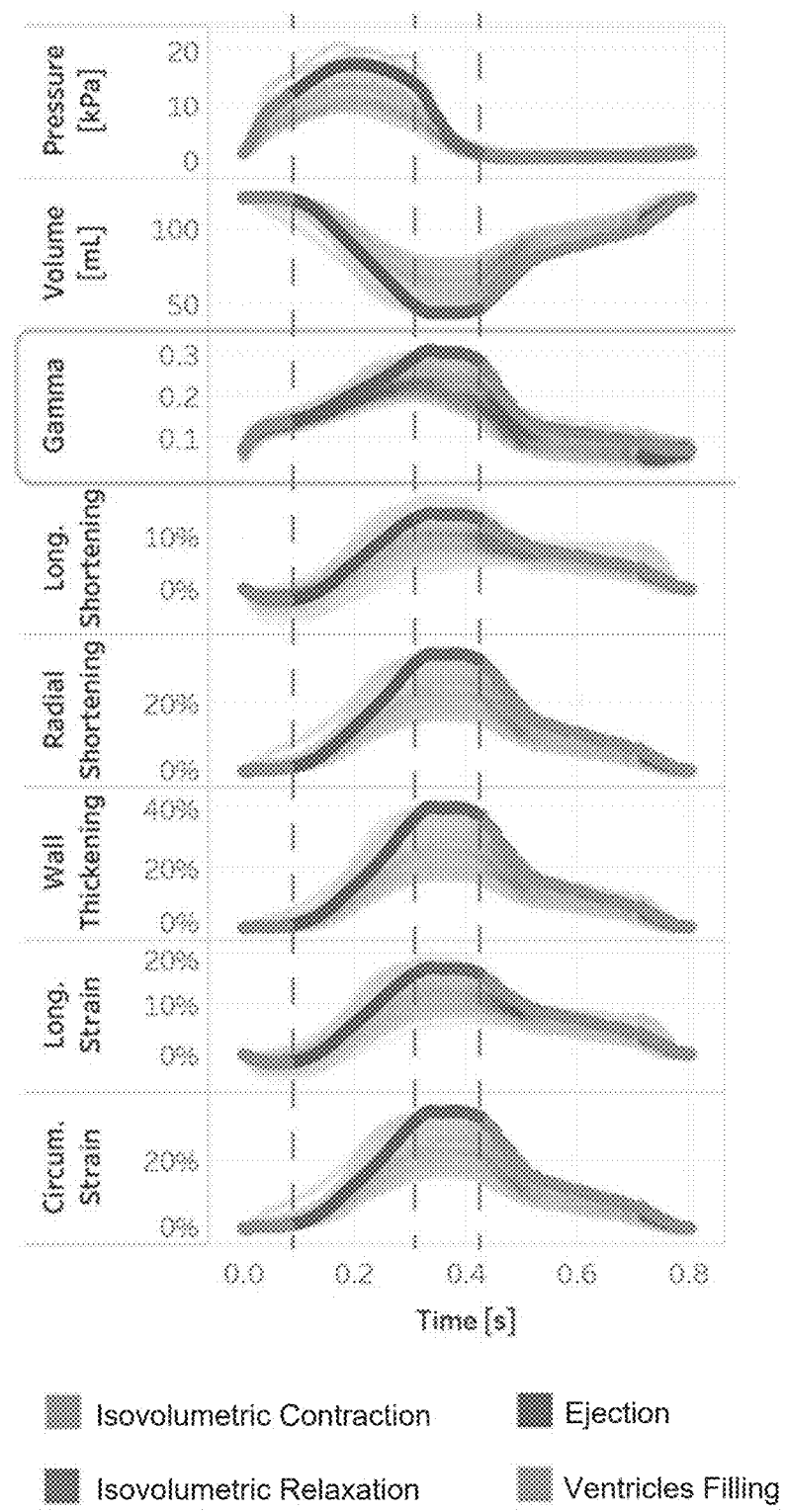
FIG. 18 illustrates temporal responses for testing of samples of a) idealized geometries in a cardiac cycle and b) patient-specific geometries in a cardiac cycle.
Figure 18:
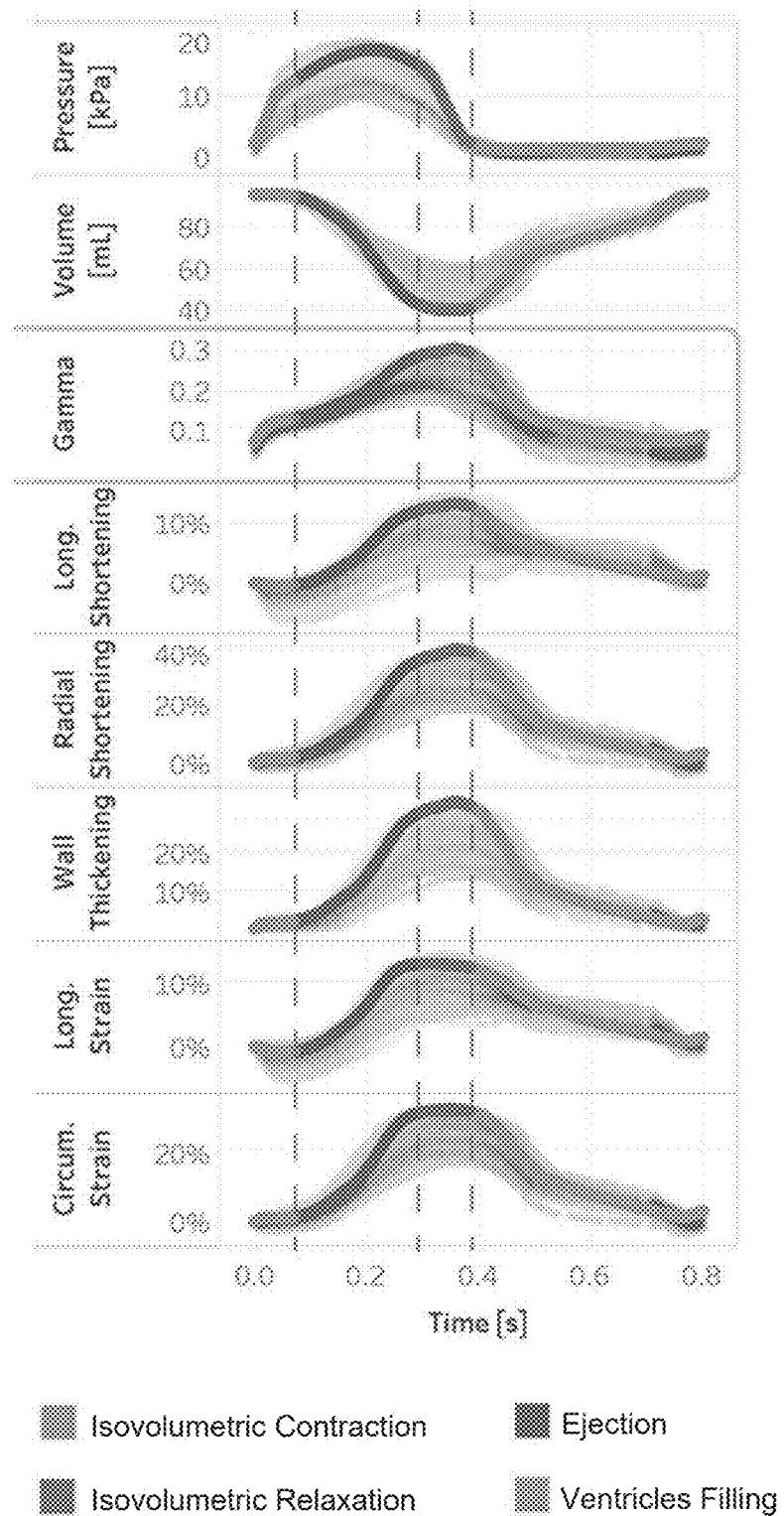

FIG. 18 illustrates the relationship of pressure and volume waveforms contrasted with gamma waveform and clinical metrics obtained from the FE simulations for an entire cardiac cycle. The data reflect results from the testing dataset for idealized (see FIG. 18a) and patient-specific (see FIG. 18b) geometries, with grayed density plots illustrating tested ranges and a highlighted sample result with colors indicating isovolumetric contraction, ejection, isovolumetric relaxation, and diastolic filling phases in a cardiac cycle. As observed, the gamma waveform has a positive relationship with pressure and a negative relationship with volume. Gamma rises as pressure increases and volume decreases. Furthermore, peak gamma is more correlated with peak volume than peak pressure. These findings are consistent with the findings of the correlation matrix. Furthermore, we can see that all clinical metrics have roughly positive associations with the gamma waveform. The general trends are tightly paired for both idealized and patient-specific scenarios.

Figure 19:
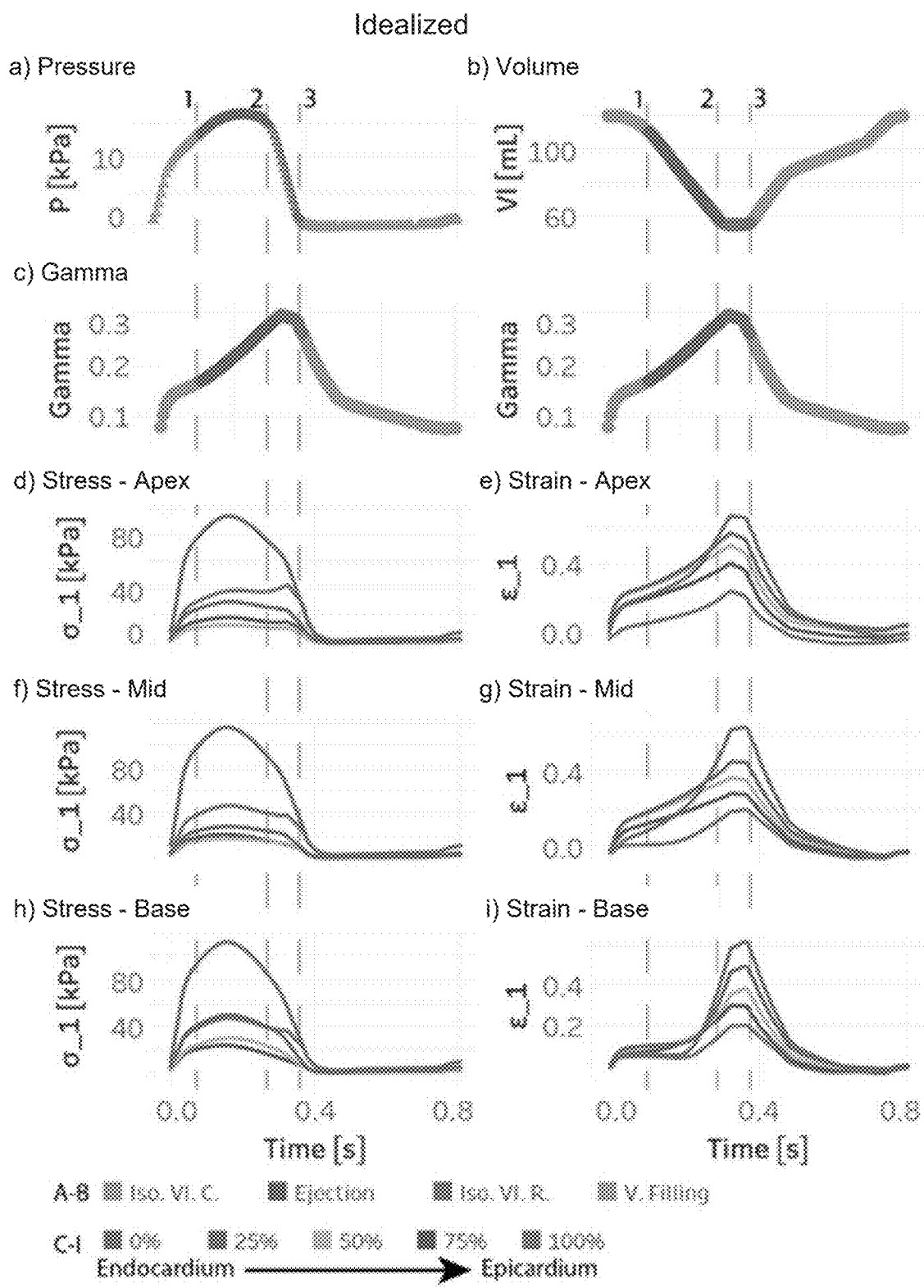
FIG. 19 illustrates maximum principal stress and strain distributions of a cardiac cycle for an idealized scenario; a) shows an input pressure waveform, b) shows an extracted volume waveform, c) shows a gamma waveform, d) shows averaged stress values for an apex region during the cardiac cycle, e) shows averaged strain values for the apex region during the cardiac cycle, f) shows averaged stress values for a mid region during the cardiac cycle, g) shows averaged strain values for the mid region during the cardiac cycle, h) shows averaged stress valves for a base region during the cardiac cycle, i) shows averaged strain values for a base region during the cardiac cycle, j) illustrates detailed stress distributions at three instances (0.11 s, 0.30 s, and 0.39 s) during the cardiac cycle, and k) illustrates detailed strain distributions at three instances (0.11 s, 0.30 s, and 0.39 s) during the cardiac cycle.
Figure 19:
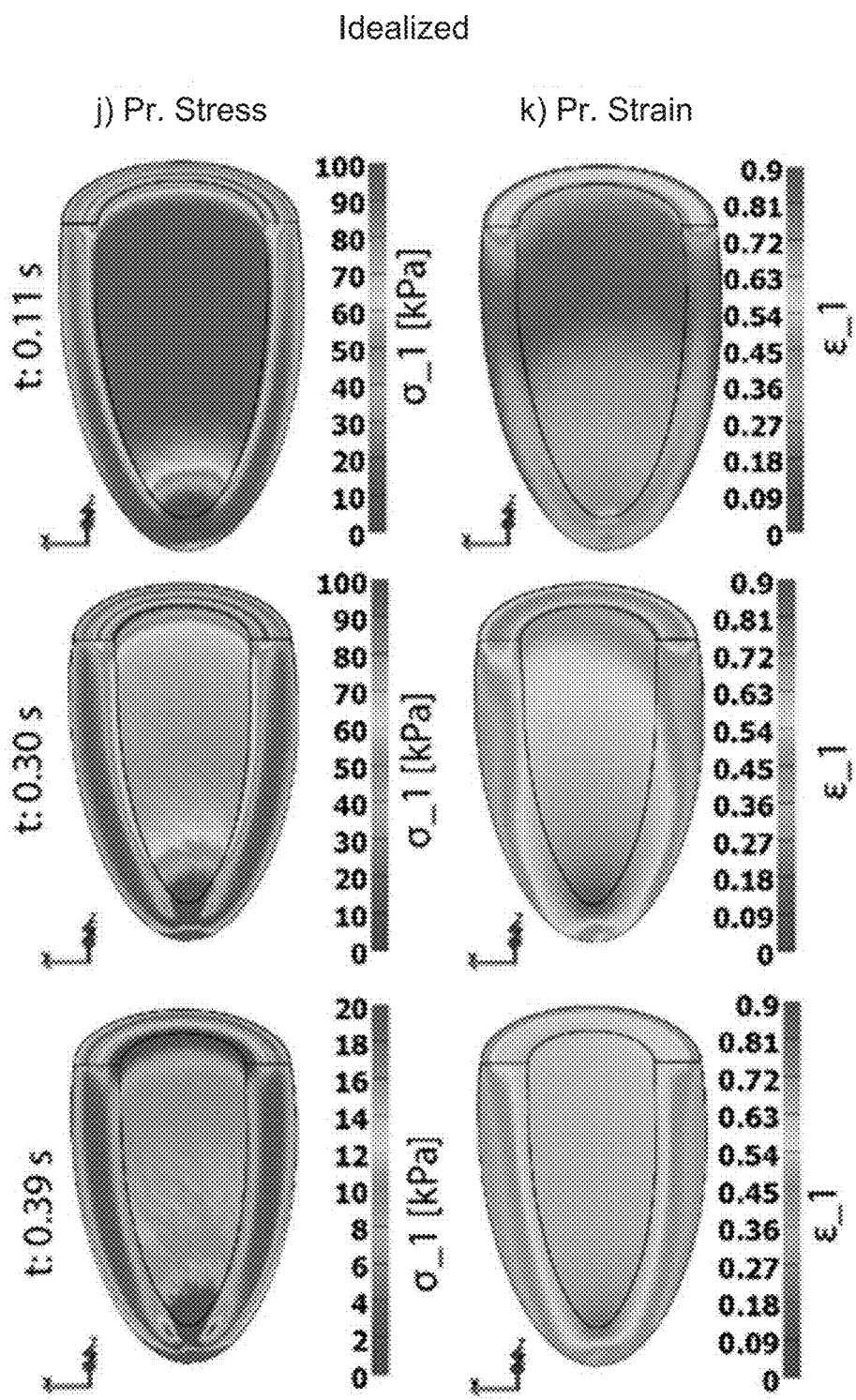
Figure 20:
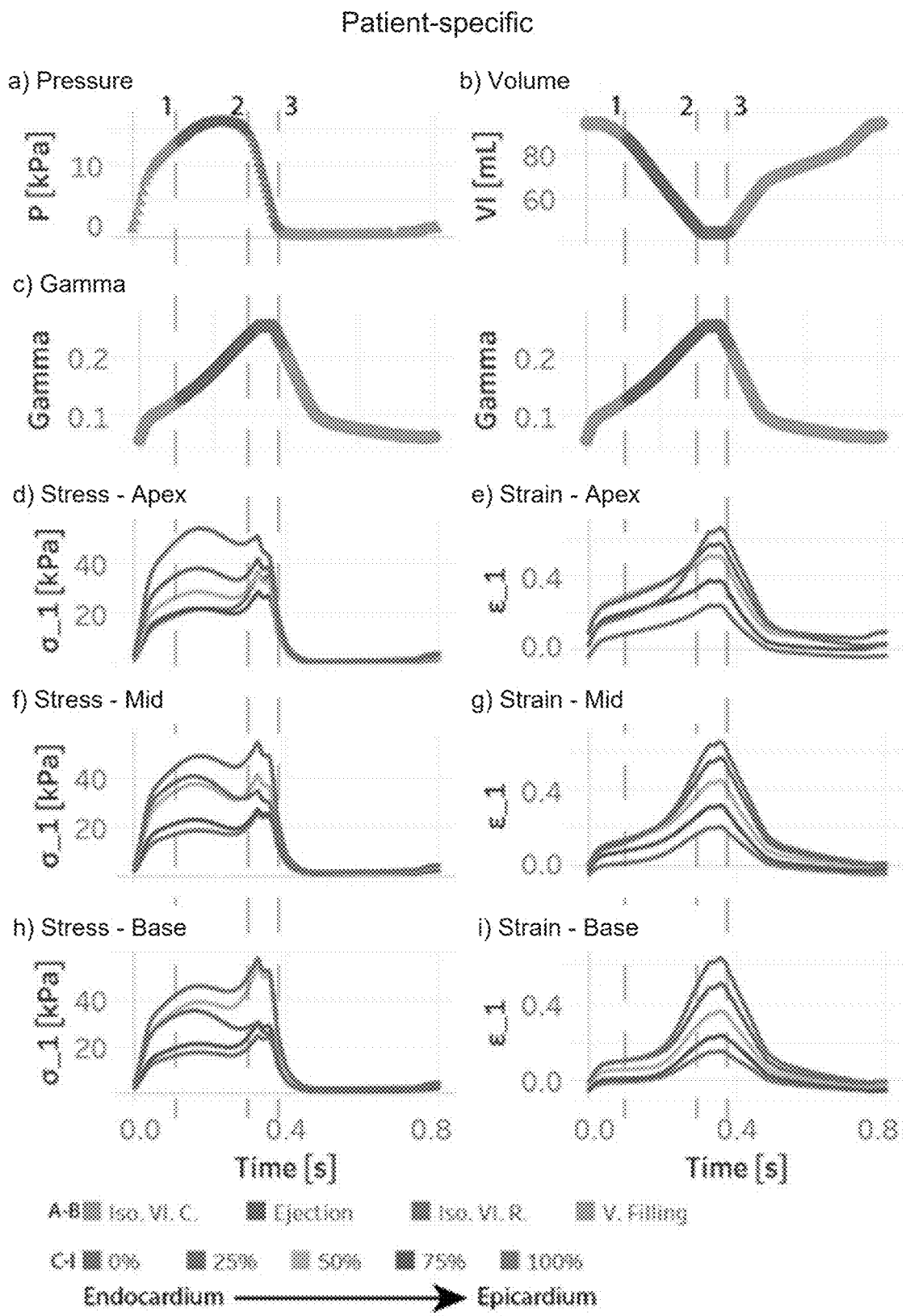
FIG. 20 is similar to FIG. 19 and illustrates maximum principal stress and strain distributions of a cardiac cycle for a patient-specific scenario; a) shows an input pressure waveform, b) shows an extracted volume waveform, c) shows a gamma waveform, d) shows averaged stress values for an apex region during the cardiac cycle, e) shows averaged strain values for the apex region during the cardiac cycle, f) shows averaged stress values for a mid region during the cardiac cycle, g) shows averaged strain values for the mid region during the cardiac cycle, h) shows averaged stress valves for a base region during the cardiac cycle, i) shows averaged strain values for a base region during the cardiac cycle, j) illustrates detailed stress distributions at three instances (0.11 s, 0.30 s, and 0.39 s) during the cardiac cycle, and k) illustrates detailed strain distributions at three instances (0.11 s, 0.30 s, and 0.39 s) during the cardiac cycle.
Figure 20:
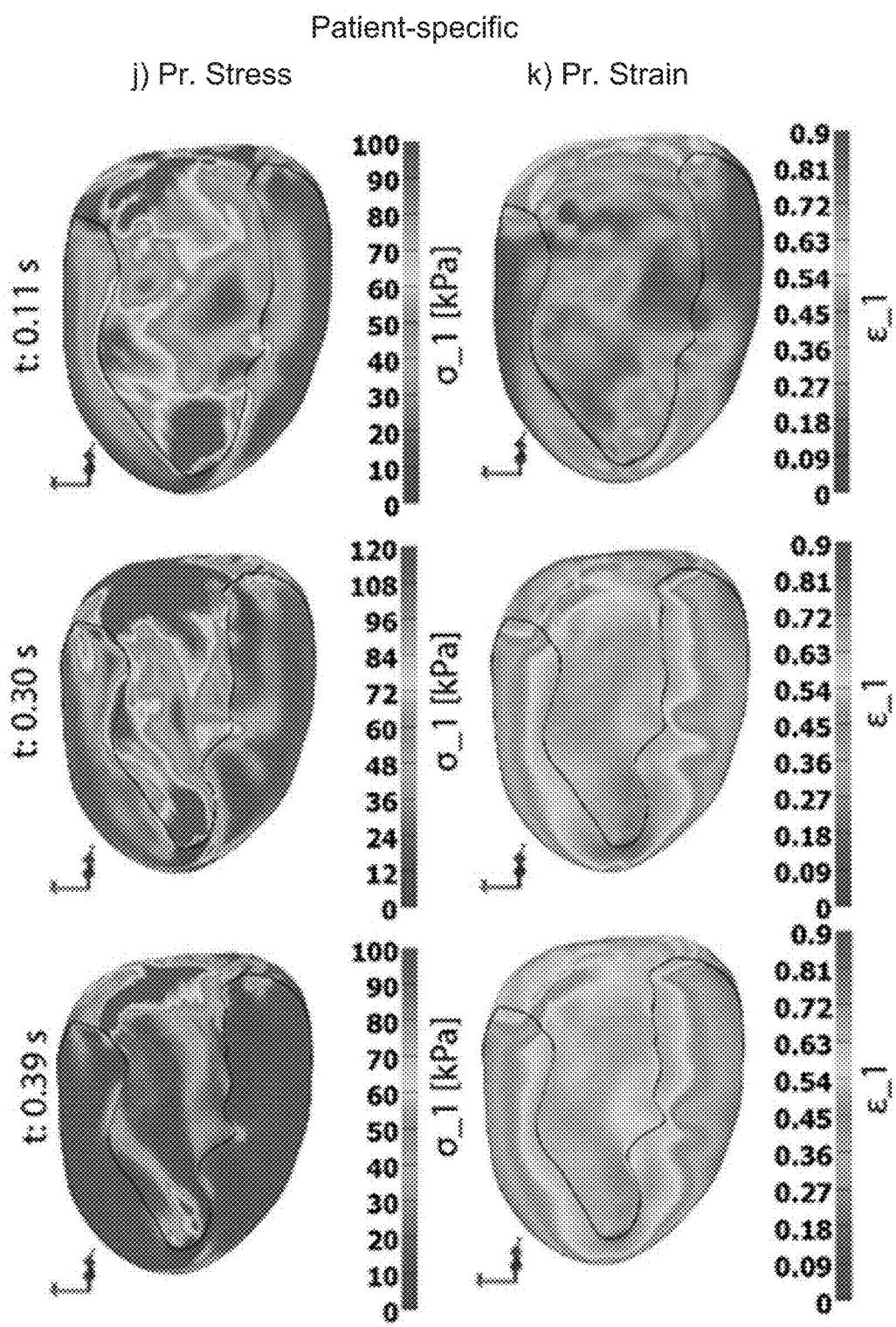

Furthermore, FIGS. 19 and 20 illustrate the principal stress (pr. stress) and principal strain (pr. strain) responses for idealized (FIG. 19) and patient-specific (FIG. 20) geometries, respectively, for a sample PV loop. Clinical metrics representing a healthy subject were used as inputs for the DL model. Measurements of pr. stress and pr. strain were taken at cross-sections of the myocardium at the apex, middle and base regions. Details on the selected regions are discussed below with respect to FIG. 25. Each cross-section was divided into five sub-sections based on radial distance, indicating regions at a specific thickness of the ventricular wall with values closer to the endocardium (0%), mid-wall (50%), and epicardium (100%). All values of each sub-region were averaged out for each time step, providing temporal responses illustrated in FIG. 19a-i and FIG. 20a-i. Additionally, the overall pr. stress and pr. strain distributions for critical time instances are shown in FIGS. 19j, 19k, 20j, and 20k.

The findings in FIGS. 19 and 20 demonstrate a direct association between the pressure waveform and principal stress levels. As pressure rises, so does pr. stress. Similar conclusions can be obtained from the volume waveform and principal strain values. This behavior is similar for all cross-sections and, consequently, exhibited throughout the entire geometry. Furthermore, from FIGS. 18-20, we can see that the gamma waveform is closely related to strain, indicating that stronger active contraction leads to higher strain values. In general, stress and strain decrease from the endocardium to the epicardium. Further, strain distribution does not change during the isovolumetric relaxation phase, but stress decreases. In addition, it is noticeable that during the ventricular filling phase, pr. stress is minimal, while pr. strain is still recovering from its peak value at isovolumetric relaxation. This is a result of non-zero active contraction during the filling phase, which regulates the ventricle deformation when the pressure is minimal.

Figure 21:
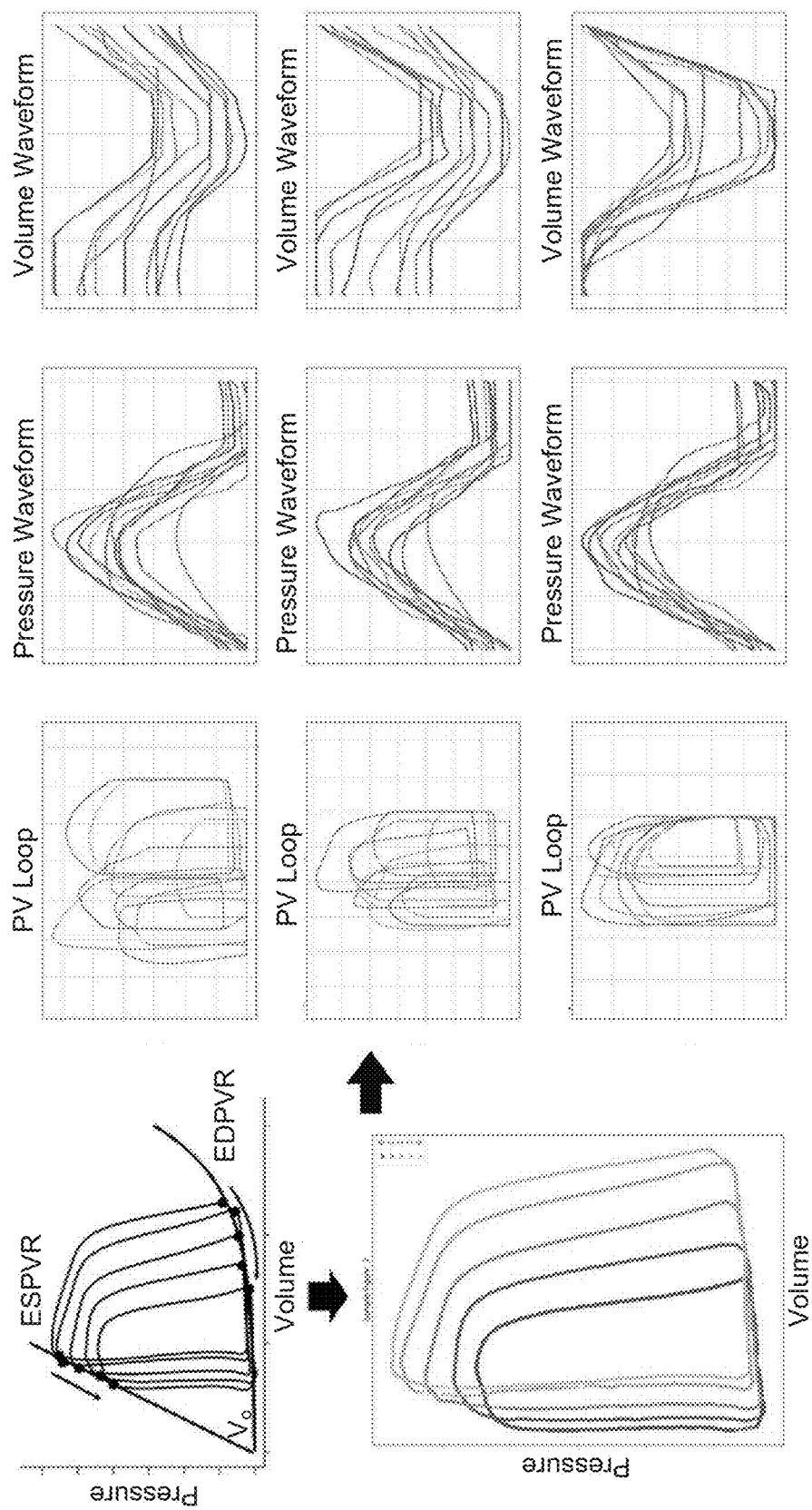
FIG. 21 illustrates exemplary graphs created based on typical point-wise data extraction from PV loops found in literature.

FIG. 21 illustrates exemplary graphs created based on typical point-wise data extraction from PV loops found in literature. The extracted data can be scaled in both dimensions using the figure's maximal reference point. This data can be augmented with an algorithm that is randomly scaled, translated, and mutates a given PV curve in both dimensions using parameters from a provided set of defined conditions.

Figure 22:
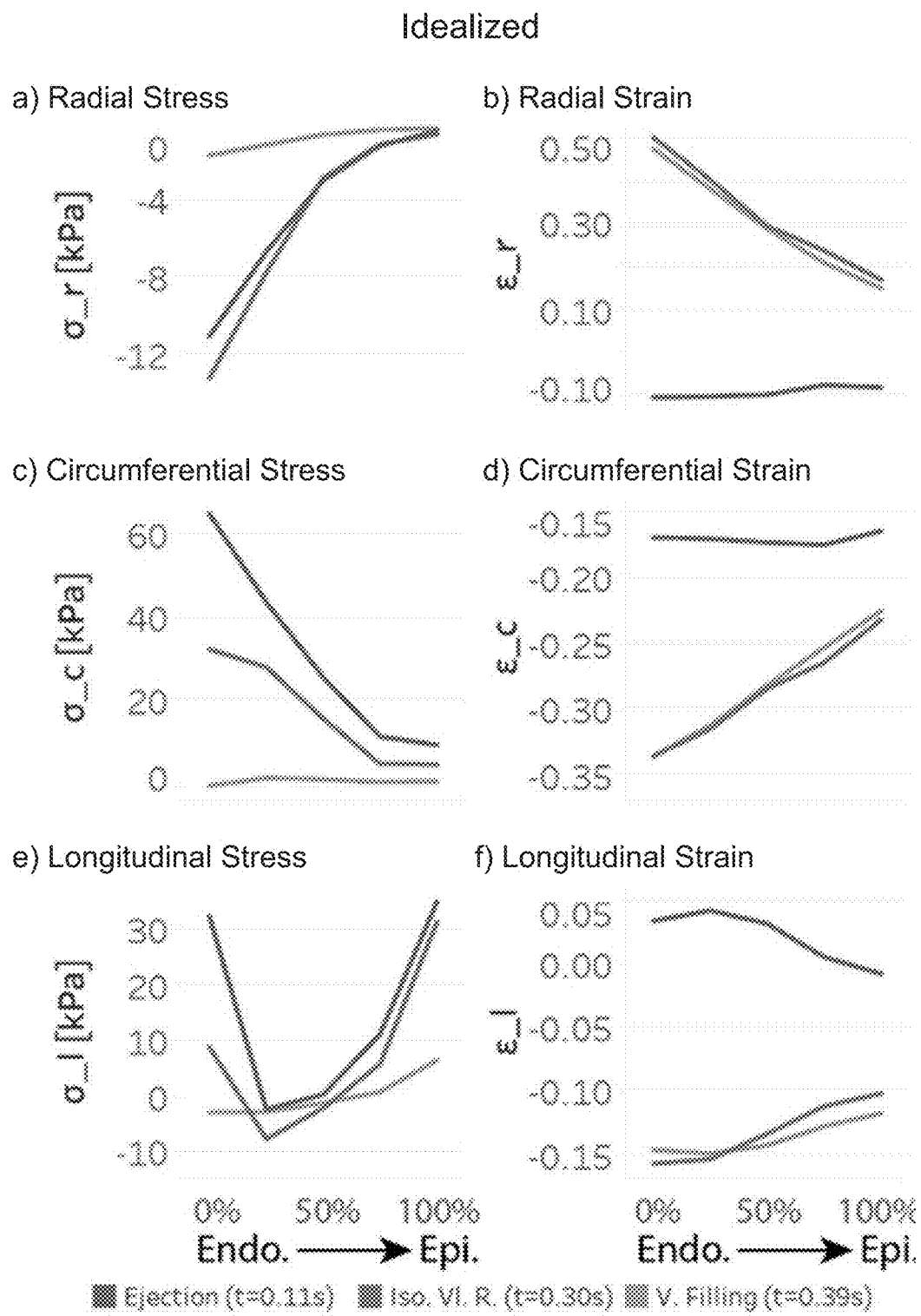
FIG. 22 shows stress and strain data for three instances of a cardiac cycle (ejection at t=0.11 s, isovolumetric relaxation at t=0.30 s, and ventricles filling at t=0.39 s) for an idealized model; a) shows stress data in a radial direction, b) shows strain data in the radial direction, c) shows stress data in a circumferential direction, d) shows strain data in the circumferential direction, e) shows stress data in a longitudinal direction, f) shows strain data in the longitudinal direction.
Figure 23:
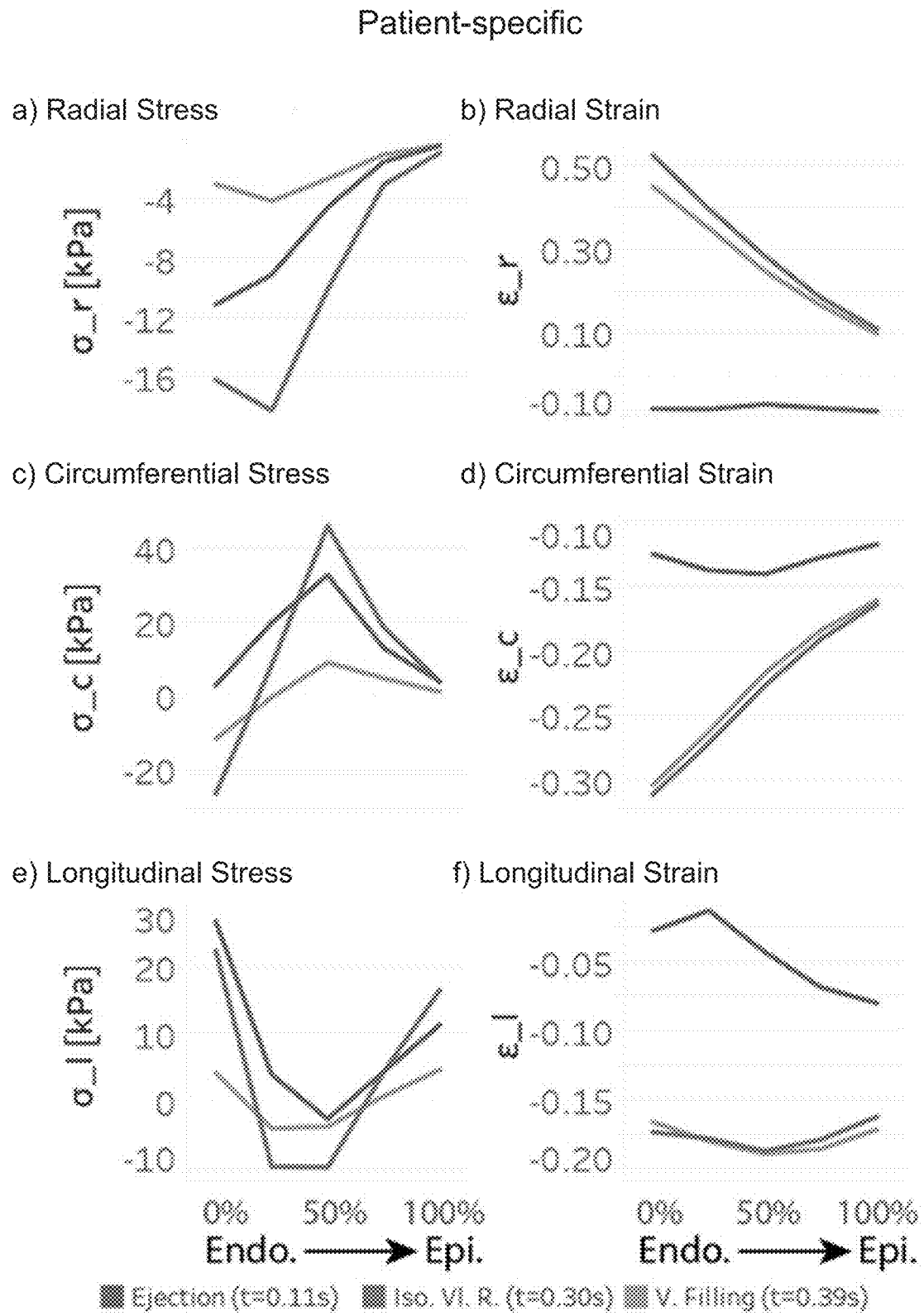
FIG. 23 is similar to FIG. 22 and shows stress and strain data for three instances of a cardiac cycle (ejection at t=0.11 s, isovolumetric relaxation at t=0.30 s, and ventricles filling at t=0.39 s) for a patient-specific model; a) shows stress data in a radial direction, b) shows strain data in the radial direction, c) shows stress data in a circumferential direction, d) shows strain data in the circumferential direction, e) shows stress data in a longitudinal direction, f) shows strain data in the longitudinal direction.

FIGS. 22 and 23 illustrate stress and strain distributions transmurally (from endocardium, 0%, to epicardium, 100%) in radial, circumferential and longitudinal directions for both idealized (FIG. 22) and patient-specific (FIG. 23) cases. Moreover, the figures depict values for the base region of the myocardium at specific time instances from three main phases of the cardiac cycle. Additional details of the selected base region are described below with reference to FIG. 25.

Figure 26:
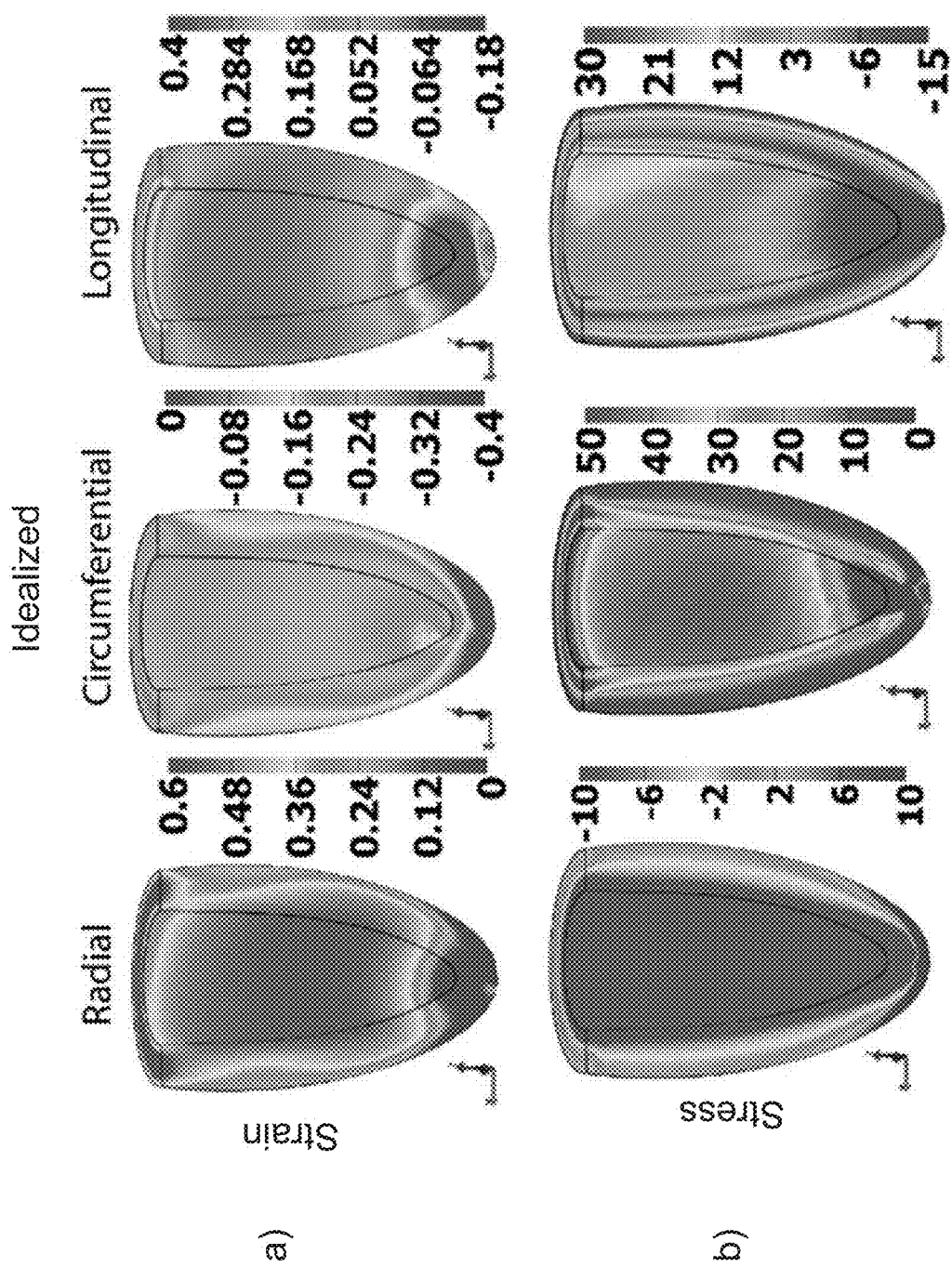
FIG. 26 shows a) strain and b) stress distributions for an idealized model at end-systole.
Figure 27:
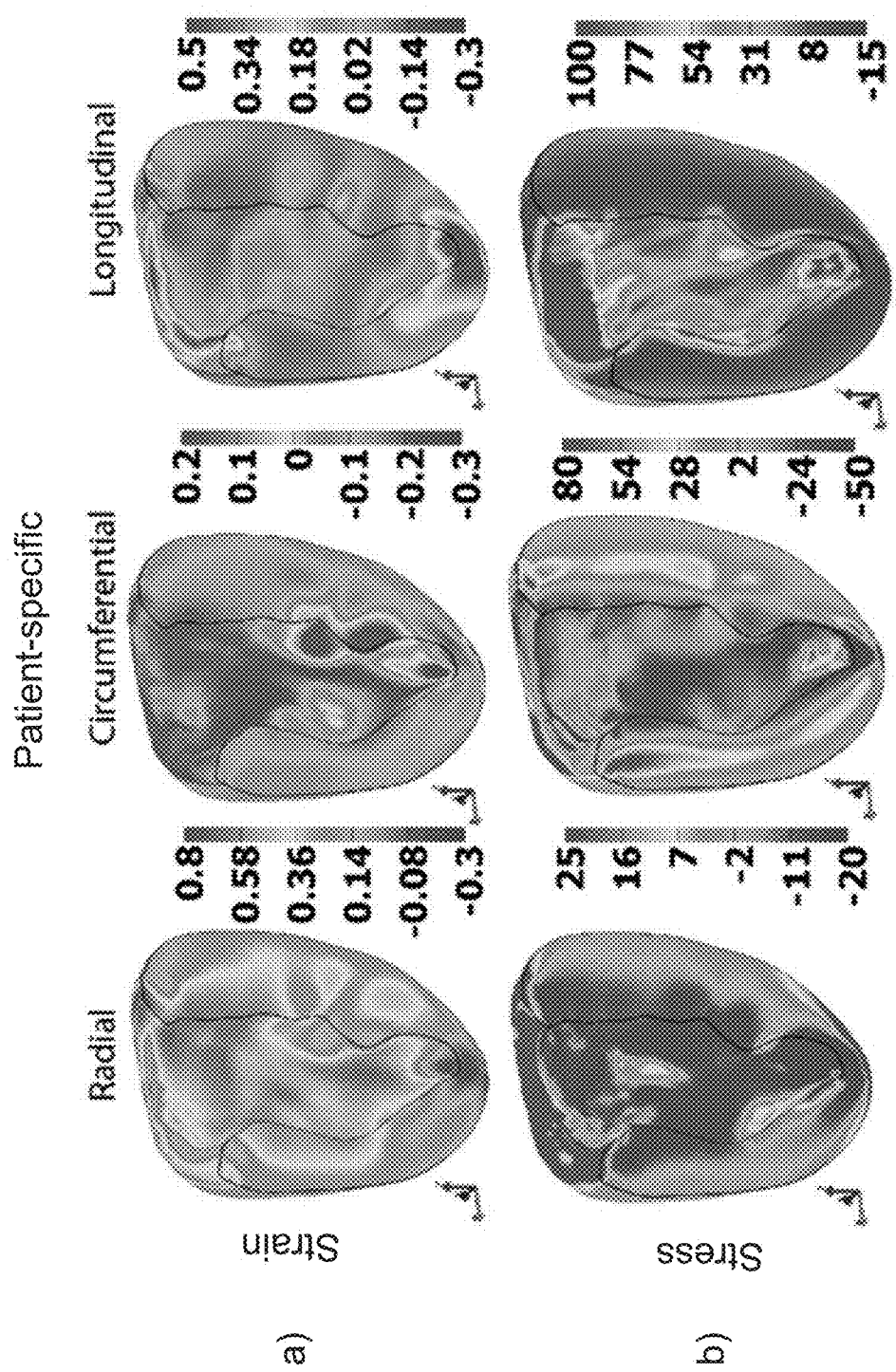
FIG. 27 shows a) strain and b) stress distributions for a patient-specific model at end-systole.

In addition, detailed stress and strain distributions for given directions at end-systole can be found in FIGS. 26 and 27. Results for FIGS. 22 and 23 were taken from the same simulations as FIGS. 19 and 20, representing similar cardiac phases for this analysis.

As observed, compressive radial stress at the endocardium generally decreases to approximately zero at the epicardium in all given instances. Similarly, the radial strain has a higher strain at the endocardium in contrast to the epicardium, with exception of the ejection phase, which remains mostly constant. Moreover, circumferential stress differs from idealized to patient-specific scenarios. There is a general decrease from endocardium to epicardium in ejection and isovolumetric contraction phases for the idealized geometry; in contrast, there is a higher circumferential stress concentration around mid-wall for patient-specific geometry. Interestingly, a similar pattern is observed for circumferential strain in both geometries.

Lastly, similar behavior for both longitudinal stress and strain is observed between the two geometries. In general, there is a "u-shaped" longitudinal stress curve, with lower values around mid-wall. Nonetheless, idealized geometry indicates higher stress at the epicardium in contrast to the endocardium at isovolumetric contraction, while patient-specific shows the opposite behavior. It is worth noting that the strain displayed here is the total strain, whereas the stress is the passive stress. The "discrepancy" between the negative strain and positive stress is the result of a large negative active strain (gamma) in the fiber direction, which causes a positive strain in the radial direction to enforce isochoric behavior. Consequently, the radial strain might be positive when the radial stress is negative due to the cavity pressure.

Embodiments of the disclosure provide an example methodology to facilitate using constitutive models in clinical applications when limited data is available. By streamlining the process of extracting constitutive model parameters directly from basic clinical measures, our technique helps to bridge the gap between constitutive modeling and clinical analysis, allowing the generation of constitutive models geared toward patient-specific conditions in a fast and efficient manner. The present disclosures highlights the benefits of combining deep learning techniques with constitutive models for predicting material properties in diverse clinical settings when access to cardiac images is limited or suffers from poor quality at different timesteps in a cardiac cycle. Moreover, embodiments of the present disclosure provide example systems and methods to predict fiber orientations under patient-specific conditions.

As input, our deep learning model incorporates a combination of basic clinical parameters that can be easily gathered from clinical imaging techniques and a PV loop. In contrast to other conventional approaches, the selection of these clinical parameters improves the model's usability for two example reasons: (a) they may only require measurements in two timesteps (end-systole and end-diastole); and (b) once computed, they are convenient to manipulate and share across diverse channels of distribution because they are simple numerical values and do not depend on positional factors imposed by complex data structures. For instance, other conventional methodologies require at least 51 strain measurements in longitudinal, radial, and circumferential directions for each time point of the PV loop to compute parameter personalization. This vast amount is cumbersome and lacks efficiency.

Further, once trained, our model effectively yields a parametric curve associated with the intensity of active LV contraction and fiber orientations at the endocardium and epicardium in a simple forward pass. These outputs may then be used to generate constitutive modeling of the LV in a patient-specific manner for further analysis. In contrast, other approaches, such as inverse parameter optimization, often require multiple optimization routines that lead to the final selection of parameters. It is worth noting that other literature does not mention the capacity to forecast fiber orientations, which can be an advantage of our method. Additionally, a close examination of the findings indicates that, with an overall MAE of 0.94 mL for the cavity volume, our model can precisely replicate the expected contraction behavior of, for instance, the left ventricular myocardium for both ideal and patient-specific cases. In addition, our findings imply a close agreement between the true and predicted values of clinical metrics, with an overall MAE of 0.7%, revealing that our deep learning model can mold the contraction response to match the intended reaction.

The observed temporal trends in FIG. 18 are consistent with the anticipated cardiac activity. Due to the double helical configuration of myocardial fibers, the LV base shifts toward the apex, shortening the LV longitudinally during systolic ventricular contraction. This motion induces a rise in LS and LST values with rising pressure during the ejection phase, peaking near the end-systole. A clinical evaluation of LST illustrates this trend for a full cardiac cycle with peak values around 22.9%. In comparison, a study conducted with healthy volunteers indicates a peak LS of 19.07%. Moreover, it is important to note that there is considerable variation in clinical reports for LST. For instance, some studies have reported a LST of 19.6%+/−2.4%, while others reported 21.1%+/−2.1%, and 25.4%+/−2.1%. Our findings reveal a similar pattern across all analyzed FE simulations: LS and LST rise with increasing pressure throughout the ejection phase, reaching maximum at end-systole. Nevertheless, it is notable that our FE models, in some embodiments, may underestimated the LS and LST values reported for healthy individuals, peaking around 18% and 13%, respectively, for the patient-specific case.

Moreover, this longitudinal shortening renders the thickening of the LV walls, which forces the endocardium inward and reduces the capacity of the left ventricular chamber. This trend is seen in our tested FE models, where wall thickness rises during the ejection phase while cavity volume decreases and reduces progressively throughout the ventricles filling phase when the volume gradually increases. The healthy WT values range between 47.4% and 91%, with a mean of 69.2%+/−21.8%, according to some studies. As observed, although WT values for the patient-specific geometry are higher than those for the idealized geometry, our overall results are relatively lower than the reported healthy condition, while some results are almost on the borderline of the lower range of clinical values for WT. Nonetheless, our values are similar to the WT reported in other simulations, which is approximately 40% for an idealized ventricle with an active stress model.

In general, ventricular motion can causes a rise in absolute circumferential strains during systole and the restoration during diastole. Similar tendencies can be found in our FE simulations: longitudinal and circumferential strains reach their respective peaks during systole, followed by a decline during diastole. CST values for idealized geometry reflect expected values for endocardium measurements in healthy subjects reported in one study 34.2%+/−4.1%, while the patient-specific scenario reaches relatively lower values closer to 29%, which are comparable to a CST of 21.6%+/−3.9% reported in another study. It is worth noting that lower values for CST are comparable to healthy patients reported in some studies, which is in the range of 14.7%+/−2.3%.

In some embodiments, the stress and strain distributions of our FE simulations reveals a direct relationship between the input PV loop and the gamma waveform. As pressure rises, so does active contraction, resulting in an increase in the stress and strain, as shown in FIGS. 19 and 20. This behavior is roughly exhibited throughout the entire geometry. The greatest reduction in principal stress occurs at end-systole, and it remains relatively low throughout the isovolumetric relaxation and ventricular filling phases. Similar to conventional findings, strain components are often raised at the apex and increased in the endocardium, as shown in FIGS. 19e, 19g, 19i and FIGS. 20e, 20g, 20i. Furthermore, some studies stated that subendocardial strains outweighed subepicardial strains, which are in line with our findings that show strain all increased from the LV base to the apex.

The results from our radial, circumferential and longitudinal strains for the idealized geometry during isovolumetric contraction, shown in red in FIGS. 22b, d, f are comparable with findings from an ideal case. Our example findings show that radial strain decreases from the endocardium to the epicardium with all positive values. Moreover, their compressive circumferential strains decrease from approximately −0.22 at the endocardium to approx. −0.1 at epicardium, while ours decrease similarly from −0.34 to −0.24; although values differ numerically, which may be due to the selection of material parameters and fiber orientations, the general trend is similar. In addition, our longitudinal strains follow a similar pattern to exemplary ideal results (e.g., from literature).

Further, strain values along the mid-wall (50%) of the patient-specific myocardium at the ejection phase, shown in red in FIGS. 23b, d, f, are comparable with experimental-derived results from literature. The tensile radial strain for the mid-layer at the base region is approximately 0.30 (FIG. 23) at ejection phase, while we observe an overall increase towards the middle region (FIG. 27), indicating the thickening of the LV walls. In contrast, negative values are observed in both circumferential and longitudinal strains, indicating ventricle contraction.

Figure 24:
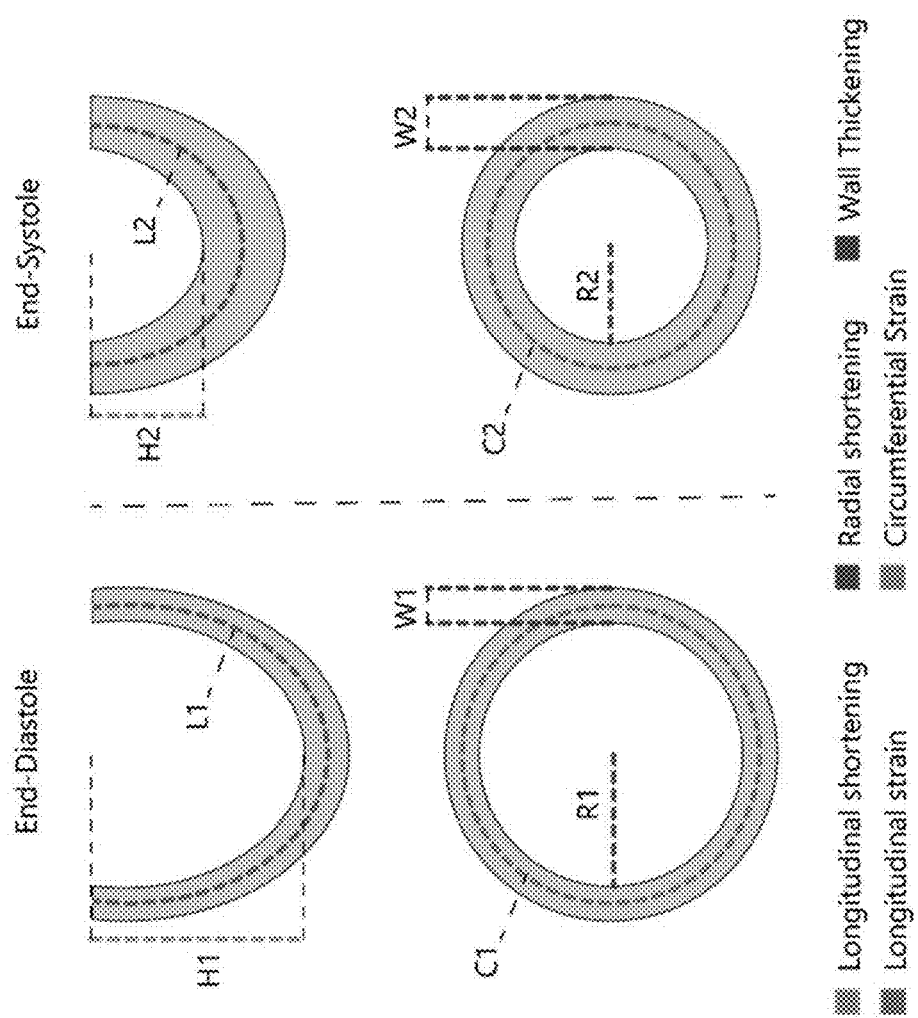
FIG. 24 shows exemplary clinical metrics computations.

In examples described herein, we considered the following example clinical metrics: longitudinal shortening (LS), circumferential shortening (CS), wall thickening (WT), longitudinal strain (LST), and circumferential strain (CST). FIG. 24 illustrates how these clinical metrics can be obtained based on geometric characters.

In general, the final clinical metrics are computed based on the difference between geometric values at end-diastole (reference configuration) and end-systole as shown, $$\frac{\mu_{end-diastole} - \mu_{end-systole}}{\mu_{end-diastole}} \quad (5)$$

where µ represents the given metric. All metrics used for deep learning model were average across all regions. In addition, we report values for the shortening and longitudinal strains as positive.

In one embodiment, the FO layer's primary function is to determine the optimal set of fiber orientations that are considered fixed parameters for the entire cardiac cycle, as these are not expected to suffer radical changes in short periods of time. Nonetheless, this process may still benefit from pertinent information from the PV loop. In theory, it could be derived through typical PV loop analyses, such as stroke volume, end-diastole, and end-systole pressure-volume, etc. However, because in one example the entire PV loop is expected to be supplied, we can treat it as a static signal with two channels for which convolutional layers are ideal for extracting features autonomously that better characterize the shape and values of the PV loop. Moreover, to ensure these features represent distinct PV loops, we treat this part of the network as an encoder and train it separately in a similar manner as the principal component analysis (PCA) approach, in which a decoder is used to reconstruct the PV loop with generated set of codes, ensuring the characterization of PV loop.

On the other hand, the purpose of the GW layer is to estimate a continuous gamma waveform that embeds temporal relationships presented in a pressure waveform—the gamma waveform, in some embodiments, must have the exact temporal resolution as the pressure waveform. Due to their internal memory, recurrent neural networks (RNNs) may retain critical information about the stimulus they receive, enabling the network to develop a more sophisticated grasp of a sequence and its context. This feature makes RNN the preferred architecture for this case, which accounts for the temporal interdependencies inherent within a PV loop while addressing additional data within its sequence.

Therefore, we are effectively employing CNNs to reduce the dimension of PV loop data, which results in the loss of critical temporal correlations contained within a PV loop sequence but allows for the estimation of fiber orientations. This temporal loss is recovered as RNNs are employed to estimate a continuous gamma waveform based on the combination of PV loop data and supplementary information (fiber orientation and clinical metrics).

Figure 25:
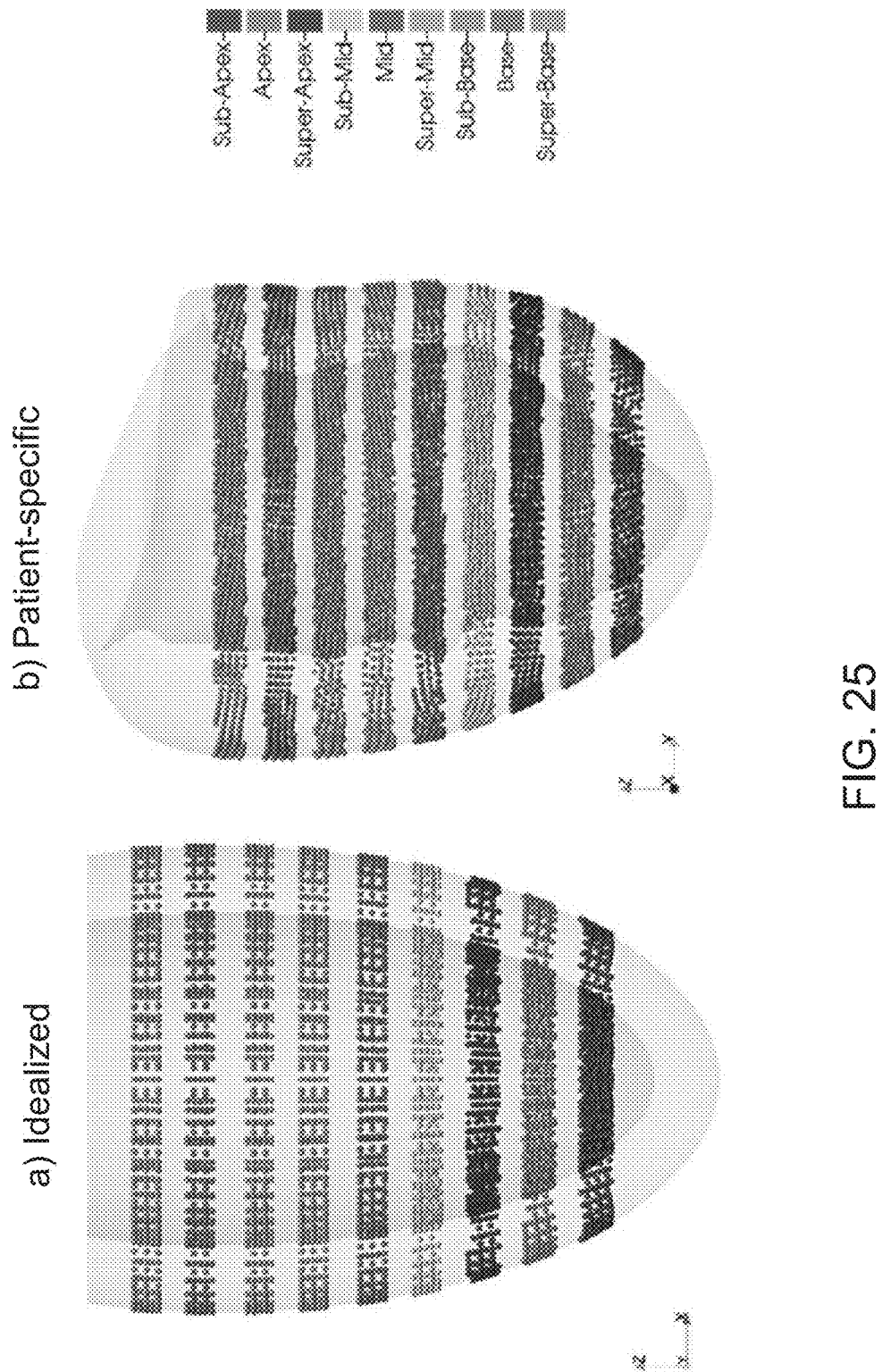
FIG. 25 shows myocardium regions for a) idealized and b) a patient-specific geometry.

In examples described herein, we considered nine regions, from the lowest region to the top-most region along the longitudinal axis: sub-apex, apex, super-apex, sub-mid, mid, super-mid, sub-base, base, and super-base. Each of these regions is distributed substantially evenly and is shown in FIG. 25.

The region distribution was based on the endocardial apex and estimated endocardial base center. To minimize inclusions of outlier values encountered at the lowest and topmost points of the LV (due to geometric factors and boundary constraints, respectively), we offset our boundaries, as shown in FIG. 25.

For further comprehension of stress and strain distribution across the myocardium wall in radial, circumferential, and longitudinal directions, FIGS. 26 and 27 show the contours of stress and strain distributions.

Constitutive modeling of hyper-elastic materials may allow for the analysis of mechanical responses of cardiac tissues; however, these models are not conventionally exploited in clinical settings owing to the complexity and unknown material properties. In contrast, deep learning models coupled with constitutive modeling allow for non-invasive clinical evaluations under patient-specific scenarios. Our research has shown that deep learning models may be efficient to retrieve model parameters based on limited data of clinical measurements. Our data generation method proved efficient in supplying a suitable training dataset for our deep learning model without the need for large patient datasets. Our deep learning model was able to accurately predict the amount of active contraction in various cardiac cycles and patient-specific settings with limited information. Further, our model was able to estimate fiber orientations at the endocardium and epicardium with minimum inaccuracy.

Embodiments of the invention may be used in a variety of systems and settings, such as healthcare systems and settings that are used measure anatomical properties, such as those of a left heart ventricle, for example. Systems and methods described herein can be employed in variety of procedures or techniques, such as a left heart ventricular angiography, coronary angiography, echocardiography, or radionuclide angiography. Furthermore, embodiments of the invention can be incorporated into a variety of medical devices, such as X-rays, computed tomography scanners, cardiac ultrasound machines, or MRI machines, for example.

Thus, examples of the disclosed technology can provide an improvement over, for instance, conventional methodologies for identifying properties of the myocardium. The previous description of the disclosed examples is provided to enable any person skilled in the art to make or use the disclosed technology. Given the benefits of this disclosure, various modifications to these examples will be readily apparent to those skilled in the art, and the generic principles defined herein may be applied to other examples without departing from the spirit or scope of the disclosed technology. Thus, the disclosed technology is not intended to be limited to the examples shown herein but is to be accorded the widest scope consistent with the principles and novel features disclosed herein Unless otherwise specified or limited, the terms "about" and "approximately," as used herein with respect to a reference value, refer to variations from the reference value of +15% or less, inclusive of the endpoints of the range. Similarly, the term "substantially," as used herein with respect to a reference value, refers to variations from the reference value of #5% or less, inclusive of the endpoints of the range.

Also as used herein, unless otherwise limited or defined, "or" indicates a non-exclusive list of components or operations that can be present in any variety of combinations, rather than an exclusive list of components that can be present only as alternatives to each other. For example, a list of "A, B, or C" indicates options of: A; B; C; A and B; A and C; B and C; and A, B, and C. Correspondingly, the term "or" as used herein is intended to indicate exclusive alternatives only when preceded by terms of exclusivity, such as "either," "one of," "only one of," or "exactly one of." For example, a list of "one of A, B, or C" indicates options of: A, but not B and C; B, but not A and C; and C, but not A and B. A list preceded by "one or more" (and variations thereon) and including "or" to separate listed elements indicates options of one or more of any or all of the listed elements. For example, the phrases "one or more of A, B, or C" and "at least one of A, B, or C" indicate options of: one or more A; one or more B; one or more C; one or more A and one or more B; one or more B and one or more C; one or more A and one or more C; and one or more of A, one or more of B, and one or more of C. Similarly, a list preceded by "a plurality of" (and variations thereon) and including "or" to separate listed elements indicates options of multiple instances of any or all of the listed elements. For example, the phrases "a plurality of A, B, or C" and "two or more of A, B, or C" indicate options of: A and B; B and C; A and C; and A, B, and C.

In some examples, aspects of the disclosed technology, including computerized implementations of methods according to the disclosed technology, can be implemented as a system, method, apparatus, or article of manufacture using standard programming or engineering techniques to produce software, firmware, hardware, or any combination thereof to control a processor device (e.g., a serial or parallel general purpose or specialized processor chip, a single- or multi-core chip, a microprocessor, a field programmable gate array, any variety of combinations of a control unit, arithmetic logic unit, and processor register, and so on), a computer (e.g., a processor device operatively coupled to a memory), or another electronically operated controller to implement aspects detailed herein. Accordingly, for example, configurations of the disclosed technology can be implemented as a set of instructions, tangibly embodied on a non-transitory computer-readable media, such that a processor device can implement the instructions based upon reading the instructions from the computer-readable media. Some examples of the disclosed technology can include (or utilize) a control device such as an automation device, a special purpose or general purpose computer including various computer hardware, software, firmware, and so on, consistent with the discussion below. As specific examples, a control device can include a processor, a microcontroller, a field-programmable gate array, a programmable logic controller, logic gates etc., and other typical components that are known in the art for implementation of appropriate functionality (e.g., memory, communication systems, power sources, user interfaces and other inputs, etc.). In some examples, a control device can include a centralized hub controller that receives, processes and (re) transmits control signals and other data to and from other distributed control devices (e.g., an engine controller, an implement controller, a drive controller, etc.), including as part of a hub-and-spoke architecture or otherwise.

Certain operations of methods according to the invention, or of systems executing those methods, may be represented schematically in the FIGS. or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIGS., or otherwise disclosed herein, can be executed in different orders than are expressly illustrated or described, as appropriate for particular embodiments of the invention. Further, in some embodiments, certain operations can be executed in parallel, including by dedicated parallel processing devices, or separate computing devices configured to interoperate as part of a large system.

As used herein in the context of computer implementation, unless otherwise specified or limited, the terms "component," "system," "module," "block," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized, manufactured, installed, etc. using methods embodying aspects of the invention. Correspondingly, any description herein of particular features, capabilities, or intended purposes of a device or system is generally intended to include disclosure of a method of using such devices for the intended purposes, of a method of otherwise implementing such capabilities, of a method of manufacturing relevant components of such a device or system (or the device or system as a whole), and of a method of installing disclosed (or otherwise known) components to support such purposes or capabilities. Similarly, unless otherwise indicated or limited, discussion herein of any method of manufacturing or using for a particular device or system, including installing the device or system, is intended to inherently include disclosure, as embodiments of the invention, of the utilized features and implemented capabilities of such device or system.

Also as used herein, unless otherwise defined or limited, directional terms are used for convenience of reference for discussion of particular figures or examples or to indicate spatial relationships relative to particular other components or context, but are not intended to indicate absolute orientation. For example, references to downward, forward, or other directions, or to top, rear, or other positions (or features) may be used to discuss aspects of a particular example or figure, but do not necessarily require similar orientation or geometry in all installations or configurations.

Also as used herein, unless otherwise limited or defined, "configured to" indicates that a component, system, or module is particularly adapted for the associated functionality. Thus, for example, a ZZ configured to YY is specifically adapted to YY, as opposed to merely being generally capable of doing so.

Although the presently disclosed technology has been described with reference to preferred examples, with the benefit of this disclosure workers skilled in the art will recognize that changes may be made in form and detail to the disclosed examples without departing from the spirit and scope of the concepts discussed herein.

The invention claimed is:

1. A method for providing active contraction properties of a myocardium, the method comprising:
    inputting a plurality of clinical metrics into a deep learning model;
    inputting a representation of a cardiac cycle through a pressure-volume loop into the deep learning model, the deep learning model including a first process layer with a first intermediate output and a second process layer that receives the first intermediate output as a first intermediate input; and
    outputting one or more contraction properties of the myocardium.

2. The method of claim 1, wherein the clinical metrics are extracted from one or more medical imaging modalities.

3. The method of claim 1, wherein the clinical metrics include longitudinal shortening, radial shortening, wall thickening, longitudinal strain, circumferential strain, and ejection fraction.

4. The method of claim 1, wherein at least one contraction property includes fiber orientation.

5. The method of claim 1, wherein at least one contraction property includes a gamma waveform.

6. The method of claim 1, wherein the first process layer includes a first stage, and
    wherein the first stage receives the pressure-volume loop and treats the pressure-volume loop as a static signal with two channels and reduces the data dimension by employing a series of convolution neural network encoders to produce PV codes that represent characteristics of the pressure-volume loop.

7. The method of claim 6, wherein the first process layer includes a second stage, and
    wherein the second stage concatenates the PV codes with the clinical metrics to provide concatenated data.

8. The method of claim 7, wherein the first process layer includes a third stage,
    wherein the third stage takes the concatenated data and employs a succession of fully connected layers with local skip connections at every two layers and general skip connections to initial information at every five layers to generate a set of fiber orientations,
    and wherein the set of fiber orientations are configured as the first intermediate output.

9. The method of claim 1, wherein the second process layer includes a first stage, and
    wherein the first stage concatenates the pressure volume-loop with the clinical metrics and the first intermediate output.

10. The method of claim 9, wherein the second process layer includes a second stage, and
    wherein the second stage employs a recurrent neural network to retrieve gamma waveform as a time-distributed sequence.

11. The method of claim 1, wherein the clinical metrics are estimated from a machine learning model that has been pre-trained on a time-independent dataset of geometric characteristics.

12. The method of claim 1, wherein the pressure-volume loop is provided by a lumped parameter model that generates a broad spectrum of physiological and pathological pressure-volume loops.

13. The method of claim 1, wherein one or more of the clinical metrics or the representation of a cardiac cycle includes patient-specific data.

14. A method of data generation for training, validating, or testing a model for outputting properties of a myocardium, the method comprising:
    inputting an initial pressure-volume loop into a training model;
    inputting initial fiber orientations into the training model;
    combining pressure and volume values with fiber orientations in a first intermediate model of the training model to produce geometric characteristics to form synthetic clinical metrics;
    combining pressure and volume values with fiber orientations in a second intermediate model of the training model to generate a synthetic gamma waveform; and
    supplying the pressure-volume loop and the synthetic clinical metrics to a deep learning model of the training model.

15. The method of claim 14, further comprising:
    outputting, from the deep learning model, an estimated gamma waveform based on the pressure-volume loop and synthetic clinical metrics.

16. The method of claim 14, wherein the initial pressure-volume loop is generated pseudo-randomly.

17. The method of claim 14, wherein the pressure and volume values are taken at an end-diastolic period and an end-systolic period.

18. The method of claim 14, wherein forming the synthetic clinical metrics and generating the gamma waveform are executed in parallel.

19. A method of using a constitutive model in a clinical application when limited clinical data is available, the method comprising:
    extracting constitutive model parameters from basic clinical measures, the basic clinical measures including a pressure-volume loop and measurements in only two timesteps of a left ventricle, the constitutive model configured to correlate applied forces with a material's mechanical response by incorporating characteristics of morphology of tissue into its internal composition to provide tissue behavior analysis.

20. The method of claim 19, wherein one of the two timesteps is at an end-systole time frame and the other of the two timesteps is at an end-systole time frame.

* * * * *